US008507227B2

(12) United States Patent
Samain

(10) Patent No.: US 8,507,227 B2
(45) Date of Patent: Aug. 13, 2013

(54) METHOD OF PRODUCING SIALYLATED OLIGOSACCHARIDES

(75) Inventor: Eric Samain, Gieres (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 786 days.

(21) Appl. No.: 12/282,125

(22) PCT Filed: Mar. 7, 2007

(86) PCT No.: PCT/EP2007/052114
§ 371 (c)(1),
(2), (4) Date: May 5, 2009

(87) PCT Pub. No.: WO2007/101862
PCT Pub. Date: Sep. 13, 2007

(65) Prior Publication Data
US 2011/0014661 A1    Jan. 20, 2011

Related U.S. Application Data

(60) Provisional application No. 60/780,350, filed on Mar. 9, 2006.

(51) Int. Cl.
*C12P 19/18* (2006.01)
(52) U.S. Cl.
USPC ................ 435/97; 435/193; 435/84; 435/7.1; 435/252.3
(58) Field of Classification Search
None
See application file for complete search history.

(56) References Cited

U.S. PATENT DOCUMENTS

2009/0082307 A1* 3/2009 Samain et al. ................... 514/54

FOREIGN PATENT DOCUMENTS

| EP | 1 484 406 A1 | 12/2004 |
|---|---|---|
| WO | WO 01/104341 | 1/2001 |
| WO | WO-2005/090552 A | 9/2005 |
| WO | WO-2006/034225 A | 3/2006 |
| WO | WO 2006/034225 A2 | 3/2006 |

OTHER PUBLICATIONS

Ganguli et al. (J. of Bacteriology, vol. 176, No. 15, pp. 4583-4589, 1994).*
Blume et al. (Biochem. J. 2004, vol. 384, pp. 599-607).*
Fierfort et al. (J. of Biotech., vol. 134, 2008, pp. 261-265).*
U.S. Appl. No. 12/955,553, filed Nov. 29, 2010, Samain.
Hood et al,. "Genetic basis for expression of the major globotetraose-containing lipopolysaccharide from *H. influenzae* strain Rd (RM118)," Glycobiology, 2001, 11(11):957-967.
Broun et al., "Catalytic plasticity of fatty acid modification enzymes underlying chemical diversity of plant lipids," Science, vol. 282, pp. 1315-1317, 1998.
Witkowski et al., "Conversion of b-ketoacyl synthase to a malonyl decarboxylase by replacement of the active-site cysteine with glutamine," Biochemistry, vol. 38, pp. 11643-11650, 1999.
Seffernick et al., "Melamine disease and Atrazine chlorohydrolase: 98 percent identical but functionally different," J. Bacteriol., vol. 183, No. 8, pp. 2405-2410, 2001.
Shao et al., "Overexpression and biochemical characterization of b-1,3-N-acetylgalactosaminyltransferase LgtD from *Haemophilus influenza* strain," Rd. Biochem. Biophys. Res. Comm., vol. 275, No. 25, pp. 19060-19067, 2000.
PUBMED Accession #Q9PNG3, published on Oct. 1, 2003.
Antoine et al., "Large scale in vivo biosynthesis of globtriose and globoteraose by high cell density culture of metabolically engineered *Escherichia coli*," Biochimie, vol. 87, pp. 197-203, 2005.
Zhang et al., "Large-scale synthesis of globotriose derivatives through recombinant *E. coli*," Organic and Biomolecular Chemistry, vol. 1, pp. 3048-3053, 2003.
Preim et al., "A new fermentation process allows large-scale production of human milk oligosaccharides by metabolically engineered bacteria," Glycobiology, vol. 12, No. 4, pp. 235-240, 2002.
Bettler et al., "Production of recombinant xenotransplantation antigen in *Escherichia coli*," Biochem. Biophys. Res. Commun., vol. 302, pp. 620-624, 2003.
Office Action issued by the Examiner in U.S. Appl. No. 11/509,818 on Oct. 28, 2009.
Office Action issued by the Examiner in U.S. Appl. No. 11/509,818 on Jan. 14, 2009.
Office Action issued by the Examiner in U.S. Appl. No. 11/509,818 on Mar. 31, 2008.
Office Action issued by the Examiner in U.S. Appl. No. 11/509,818 on Jan. 23, 2008.
Gilbert et al., "Characterization of a recombinant *Neisseria menigitidis* α-2,3-sialyltransferase and its acceptor specificity," Eur. J. Biochm., vol. 249, pp. 187-194, 1997.
Martin et al., "Lewis X Biosynthesis in *Helicobacter pylori*," The Journal of Biological Chemistry, vol. 272, No. 34, pp. 21349-21356, 1997.
Dumon et al., "Production of Lewis x Tetrasaccharides by Metabolically Engineered *Escherichia coli*," ChemBioChem, vol. 7, pp. 359-365, 2006.
Antoine, et al.; "Highly efficient biosynthesis of the oligosaccharide moiety of the GD3 ganglioside by using metabolically engineered *Escherichia coli*"; Angewandte Chemie (International Ed. In English) (Feb. 18, 2005), vol. 44, No. 9, pp. 1350-1352.
Antoine, et al.; "Large-scale in vivo synthesis of the carbohydrate moieties of gangliosides GM1 and GM2 by metabolically engineered *Escherichia coli*;" Chembiochem—A European Journal of Chemical Biology, Wiley VCH, Weinheim, DE, vol. 4, No. 5 (May 9, 2003), pp. 406-412.
Hamamoto, et al.; "Enzymatic synthesis of cytidine 5'-monophospho-N-acetylneuraminic acid"; Bioscience, Biotechnology, and Biochemistry (Oct. 2005), vol. 69, No. 10, pp. 1944-1950.

(Continued)

*Primary Examiner* — Hope Robinson
(74) *Attorney, Agent, or Firm* — Foley & Lardner LLP

(57) ABSTRACT

The present invention relates to a method for the large scale in vivo synthesis of sialylated oligosaccharides, culturing a microorganism in a culture medium, optionally comprising an exogenous precursor such as lactose, wherein said microorganism comprises heterologous genes encoding a CMP-Neu5Ac synthetase, a sialic acid synthase, a GlcNAc-6-phosphate 2 epimerase and a sialyltransferase, and wherein the endogenous genes coding for sialic acid aldolase (NanA) and for ManNac kinase (NanK) have been deleted or inactivated. The invention also relates to these micoorganisms which are capable of producing internally activated sialic acid.

16 Claims, 10 Drawing Sheets

(56) References Cited

OTHER PUBLICATIONS

Endo, et al.; "Large-Scale Production of CMP-NEUAC and Sialylated Oligosaccharidesthrough Bacterial Coupling"; Applied Microbiology and Biotechnology, Springer Verlag, Berlin, DE, vol. 53, No. 3 (Mar. 2000), pp. 257-261.

Vimr et al., "Genetic Analysis of Chromosomal Mutations in the Polysialic Acid Gene Cluster of *Escherichia coli* K1," Journal of Bacteriology, vol. 171, No. 2, pp. 1106-1117, Feb. 1989.

Vimr et al., "Diversity of Microbial Sialic Acid Metabolism," Microbiology and Molecular Biology Reviews, vol. 68, No. 1, pp. 132-153, Mar. 2004.

Steenbergen et al., "Functional analysis of the sialytransferase complexes in *Escherichia coli* K1 and K92," Journal of Bacteriology, vol. 174, No. 4, pp. 1099-1108, 1992.

Vimr et al., "Regulation of Sialic Acid Metabolism in *Escherichia coli*: Role of N-Acylneuraminate Pyruvate-Lyase," Journal of Bacteriology, vol. 164, No. 2, pp. 854-860, Nov. 1985.

Ringenberg et al., "Redirection of sialic acid metabolism in genetically engineered *Escherichia coli*," Glycobiology, vol. 11, No. 7, pp. 533-539, 2001.

Schoenhofen et al., "The CMP-legionaminic acid pathway in *Campylobacter*. Biosynthesis involving novel GDP-linked precursors," Glycobiology, vol. 19, No. 7, pp. 715-725, 2009.

Schoenhofen et al., Supplemenary Information for "The CMP-legionaminic acid pathway in Campylobacter: biosynthesis involving novel GDP-linked precursors,"Glycobiology, vol. 19, No. 7, pp. 715-725, 2009.

Ringenberg et al., "The first committed step in the biosynthesis of sialic acid by *Escherichia coli* K1 does not involve a phosphorylated N-acetylmannosamine intermediate," Molecular Microbiology, vol. 50, No. 3, pp. 961-975, 2003.

* cited by examiner

METHOD OF PRODUCING SIALYLATED OLIGOSACCHARIDES

FIELD OF THE INVENTION

The present invention relates to a method for the large scale in vivo synthesis of sialylated oligosaccharides, culturing a microorganism in a culture medium, optionally comprising an exogenous precursor such as lactose, wherein said microorganism comprises heterologous genes encoding a CMP-Neu5Ac synthetase, a sialic acid synthase, a GlcNAc-6-phosphate 2 epimerase and a sialyltransferase, and wherein the endogenous genes coding for sialic acid aldolase (NanA) and for ManNac kinase (NanK) have been deleted or inactivated. The invention also relates to this micoorganism which is capable of producing internally activated sialic acid.

BACKGROUND OF THE INVENTION

N-acetylneuraminic acid (Neu5Ac) is the most common member of the sialic acid family of aminosugars. Neu5Ac is frequently found as a terminal sugar in cell surface complex carbohydrates and plays a major role in many biological processes such as cellular adhesion and binding of toxins and virus (Varki, 1993). Neu5Ac is also a major component of the carbohydrate portion of gangliosides which are notably abundant in brain tissue and are involved in several pathologies (Zhang & Kiechle, 2004).

In reason of their important biological functions, sialic acid containing oligosaccharides has attracted considerable interest and many methods have been developed to synthesize these structures for fundamental research and potential therapeutic applications. However, large scale production of sialylated oligosaccharides has not been reached as of today.

Chemical syntheses are not practical in reason of the multiple protection and deprotection steps and a lot of efforts has been put on enzymatic and biotechnological methods. Sialyltransferases use CMP-Neu5Ac as the activated sugar-nucleotide and the development of efficient processes for enzymatic syntheses of sialylooligosaccharides has been possible through the identification of bacterial sialyltransferase genes which are well expressed in *E. coli* and the design of multiple enzymatic systems that mimic the natural pathway of sugar nucleotide biosynthesis (Gilbert et al., 1998).

A significant improvement later came from the use of living bacterial cells to produce sialylooligosaccharides (Priem et al., 2002). In this approach, sialyllactose was directly produced by growing cells of metabolically engineered *Escherichia coli* strains overexpressing the *Neisseria meningitidis* genes for α-2,3-Sialyltransferase and for CMP-Neu5Ac synthase. The bacteria were grown at high cell density with glycerol as the carbon and energy source, while exogenous lactose and Neu5Ac were supplied as precursors for sialyllactose synthesis. During the growth, lactose and Neu5Ac were actively internalized by. *E. coli* β-galactoside and Neu5Ac permeases. To prevent catabolism of lactose and Neu5Ac, mutant strains devoid of β-galactosidase and Neu5Ac aldolase activities were used. Lactose and Neu5Ac accumulated in the cytoplasm where Neu5Ac was then converted into CMP-Neu5Ac to be further transferred on lactose to form sialyllactose (our European patent EP 1194584). This system was applied to the production of the carbohydrate portion of gangliosides GM2 and GM1 by additionally expressing the appropriate glycosyltransferase genes (Antoine et al., 2003). Polysialylated oligosaccharides (GD3 and GT3 sugars) were also produced by this method and with the *Campylobacter* cstII gene that encodes a bifunctional α-2,3- and α-2,8-sialyltransferase (our application U.S. 60/690,837 and Antoine et al., 2005).

Large scale production of sialylooligosaccharides by this microbiological method requires important amount of sialic acid as a precursor. Sialic acid can be purified from natural sources such as milk and egg yolk, but the yields are low and the procedure is not suitable for large scale production. Sialic acid is generally prepared by enzymatic synthesis by the sialic acid aldolase using N-acetylmannosamine (ManNAc) and pyruvate as substrate. To reduce the cost, ManNAc is usually prepared by chemical or enzymatic epimerization of N-acetylglucosamine which is a cheaper substrate than ManNAc (Lee et al., 2004; Maru et al., 1998). In spite of these improvements the sialic acid cost is still relatively high and this cost hampers the development of a economical system for the production of sialylooligosaccharides.

Also, strains like *E. coli* K1 and *N. meningitidis* are able to produce CMP-Neu5Ac but they are pathogenic and cannot be used in biotechnological processes for safety reasons. Most of other bacteria, including *E. coli* K12, do not have the enzymatic machinery for the biosynthesis of CMP-Neu5Ac, and it is a goal of the invention to genetically engineer non pathogenic strains which would be able to produce CMP-Neu5Ac from endogenous UDP-GlcNAc.

In connection with the present invention, we have designed a new microbial system for cost-effective large scale production of sialylooligosaccharides without the need of an exogenous supply of sialic acid. The metabolically engineered microorganisms of the invention are viable, non-pathogenic and can be used in large scale and industrial culture processes. They have optimized modified pathways and deletion of futile metabolic cycles and they lead to biosynthesis of activated CMP-Neu5Ac which serves as in situ sialic acid donnor to form sialylated oligosaccharides.

BRIEF SUMMARY OF THE INVENTION

The present invention provides a method of producing sialylated oligosaccharides by fermentative growth of microorganisms. In particular, the invention relates to a method of synthesis of oligosaccharides bearing one or several sialic acid residu(s), without any exogenous sialic acid addition to the culture medium, including but not limited to:

oligosaccharide moieties of the gangliosides selected from GM3 (3'sialyllactose, Neu5Acα-3Galβ-4Glc) and oligosaccharides comprising the GM3 motif, GD3 Neu5Acα-8Neu5Acα-3Galβ-4Glc
GT3 (Neu5Acα-8Neu5Acα-8Neu5Acα-3Galβ-4Glc);
GM2 GalNAcβ-4(Neu5Acα-3)Galβ-4Glc,
GM1 Galβ-3GalNAcβ-4(Neu5Acα-3)Galβ-4Glc,
GD1a Neu5Acα-3Galβ-3GalNAcβ-4(Neu5Acα-3)Galβ-4Glc
GT1a Neu5Acα-8Neu5Acα-3Galβ-3GalNAcβ-4(Neu5Acα-3)Galβ-4Glc
GD2 GalNAcβ-4(Neu5Acα-8Neu5Acα3)Galβ-4Glc
GT2 GalNAcβ-4(Neu5Acα-8Neu5Acα-8Neu5Acα3)Galβ-4Glc
GD1b, Galβ-3GalNAcβ-4(Neu5Acα-8Neu5Acα3)Galβ-4Glc
GT1b Neu5Acα-3Galβ-3GalNAcβ-4(Neu5Acα-8Neu5Acα3)Galβ-4Glc
GQ1b Neu5Acα-8Neu5Acα-3Galβ-3GalNAcβ-4(Neu5Acα-8Neu5Acα3)Galβ-4Glc
GT1c Galβ-3GalNAcβ-4(Neu5Acα-8Neu5Acα-8Neu5Acα3)Galβ-4Glc GQ1c, Neu5Acα-3Galβ-3GalNAcβ-4(Neu5Acα-8Neu5Acα-8Neu5Acα3)Galβ-4Glc GP1c Neu5Acα-8Neu5Acα-3Galβ-3GalNAcβ-4 (Neu5Acα-8Neu5Acα-8Neu5Acα3)Galβ-4Glc GD1α Neu5Acα-3Galβ-3(Neu5Acα-6)GalNAcβ-4Galβ-4Glc Fucosyl-GM1 Fucα-2Galβ-3GalNAcβ-4(Neu5Acα-3)Galβ-4Glc;

all of which may be extended to the production of the corresponding gangliosides by reacting the above oligosaccharide moieties with ceramide.

other sialylated sugars including:
  6'sialyllactose (Neu5Acα-6Galβ-4Glc) and oligosaccharides comprising 6'sialyllactose
  SGG hexasaccharide (Neu5Acα-3Galβ-3GalNacβ-3Galα-4Galβ-4Gal)
  Sialylated tetrasaccharide (Neu5Acα-3Galβ-4GlcNacβ-4GlcNAc)
  pentasaccharide $LST_D$ (Neu5Acα-3Galβ-4GlcNacβ-3Galβ-4Glc)

In one particular aspect, the process of the invention is based on the active uptake of an exogenous precursor, such as for example a mono, di or tri-saccharide, more particularly an exogenous precursor selected from lactose, galactose, β-galactoside, and α-galactoside such as globotriose (Galα-4Galβ-4Glc), while the cells are growing on an alternative carbon substrate, such as glycerol or glucose. The expression "exogenous precursor" is intended to denote a compound involved in the biosynthetic pathway of the oligosaccharide according to the invention that is internalized by the cells.

It also provides metabolically engineered microorganisms that can specifically produce the above sialylated oligosaccharides without side products such as GA1, GA2, GA3, GA4, and GA5 and to the use of the cstIII gene isolated from *C. jejuni* strains expressing lipooligosaccharide structures that mimic the GM1 ganglioside, such as the *C. jejuni* strain NCTC Accession No 111168, for the specific production of GM1.

DISCLOSURE OF ORIGIN OF GENETIC MATERIAL

TABLE 1

Figure 1:
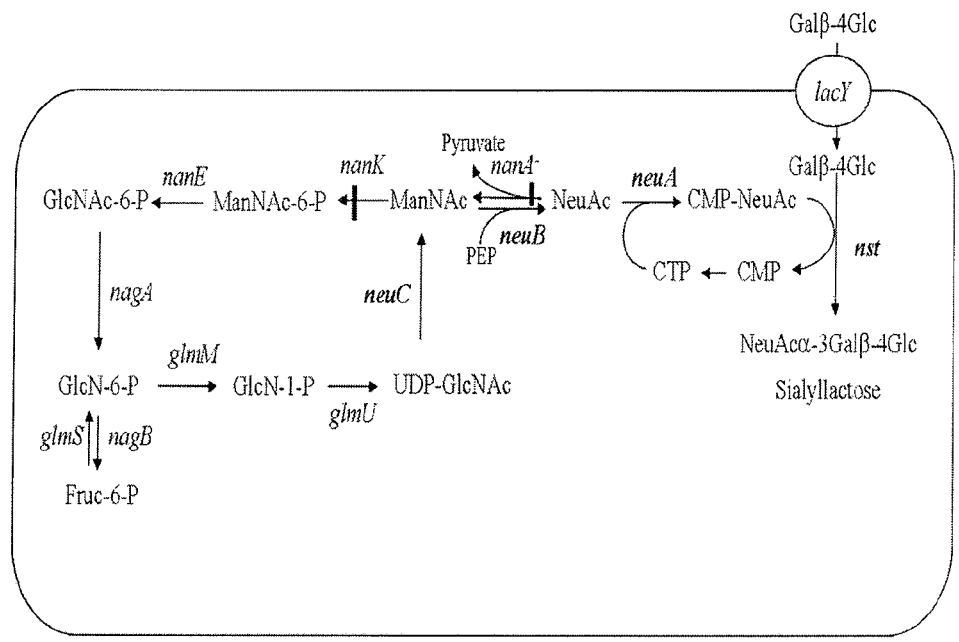
FIG. 1 shows the production of sialyllactose by metabolically engineered *E. coli* strain.

Genes, plasmids and *Escherichia coli* strains used in present invention

| | Description | Reference or source |
|---|---|---|
| Genes | | |
| nst | α-2,3-Sialyltransferase from *N. meningitidis* L3 strain MC58 | U60660 |
| neuA | CMP-Neu5Ac synthetase from *C. jejuni* strain ATCC 43438 | AF400048 |
| neuB | Sialic acid synthase from *C. jejuni* strain ATCC 43438 | AF400048 |
| neuC | GlcNAc-6-phosphate 2 epimerase from *C. jejuni* strain ATCC 43438 | AF400048 |
| cgtA | β-4 GalNAc transferase from *C. jejuni* O:19 strain OH4384 | AF130984 |
| wbpP | UDP-GlcNAc C4 epimerase from *P. aeruginosa* | AF035937 |
| gne (Cj1131c) | UDP-GlcNAc C4 epimerase from *C. jejuni* O:2 strain NCTC 11168 | AL139077 |
| cstIII (Cj1140) | α-2,3 Sialyltransferase from *C. jejuni* O:2 strain NCTC 11168 | AL139077 |
| cgtAII | β-4 GalNAc transferase from *C. jejuni* O:36 strain ATCC 43456 | AF401528 |
| cgtB (Cj1139c) | β-3 Gal transferase from *C. jejuni* O:2 strain NCTC 11168 | AL139077 |
| cstII | α-2,3 α-2,8-Sialyltransferase from *C. jejuni* strain ATCC43438 | AF400048 |
| nodC | N-acetylglucosaminyltransferase from *Azorhizobium. caulinodans* | AAB51164 |
| lgtB | β1,4-galactosyltransferase from *Neisseria meningitidis* | AAC44085 |
| chiA | chitinase from *Bacillus circulans* | AAA81528 |
| Plasmids | | |
| pWKS130 | Cloning vector, Km$^r$, Plac promoter, low copy number, pSC101 replicon | (Wang & Kushner, 1991) |
| pSU27-18 | pACYC184-derived cloning vectors Cm$^r$ P$_{lac}$ promoter, | (Martinez et al., 1988) |
| pBAD33 | pACYC184-derived cloning vectors Cm$^r$ P$_{ara}$ promoter, | Guzman et al 1995 |
| pBS-nst | pBluescript II SK derivative carrying nst (previously called NST-01) | (Priem et al., 2002) |
| pBBR1MCS-3 | Cloning vector, Tc$^r$, P$_{lac}$ promoter, low copy number, | (Kovach et al., 1995) |
| pBBR3-SS | pBBR1MCS-3 derivative carrying neuABC | present invention |
| pBBR3-SS-wbpP | pBBR1MCS-3 derivative carrying neuABC and wbpP | present invention |
| pBBR3-SS-gne | pBBR1MCS-3 derivative carrying neuABC and gne | present invention |
| pUC-cstII | pUC18 derivative carrying cstII | present invention |
| pBS-cgtAII-nst | pBluescript II SK derivative carrying cgtAII and nst | present invention |
| pBS-cgtA-cstII | pBluescript II KS derivative carrying, cgtA, cstII | present invention |
| pSU18-cgtB | pSU27 18 derivative carrying cgtB | present invention |
| pBS-cstIII-cgtAII | pBluescript II KS derivative carrying, cstIII and cgtAII | present invention |
| pWKS-cgtAII | pWKS130 derivative carrying cgtAII, | present invention |
| pBAD33-cgtAII | pBAD33 derivative carrying cgtAII, | present invention |
| pWKS-lgtB-chiA | pWKS130 derivative carrying nst and the chitinase chiA | (Dumon et al., 2005) |
| pBS-nst-nodC | pBluescript II SK derivative carrying *A. caulinodans* nodC and nst | present invention |
| pBS-cstII-cgtB | pBluescript II KS derivative carrying cstII and cgtB | present invention |
| Strains | | |
| DC | DH1 lacZ lacA | (Dumon et al., 2005) |
| GLK | DH1 lacZ lacA galK | (Dumon et al., 2005) |
| ZLKA | DC ΔnanKETA | present invention |
| AZL | DC nanA | present invention |
| AZK | DC ΔnanK nanA | present invention |
| ZWU | ZLKA galU | present invention |
| GLKA | GLK ΔnanKETA | present invention |
| ZW | ZLKA melA wcaJ | present invention |
| DC6 | DC (pBS-nst, pBBR3-SS) | present invention |
| AW1 | AZL (pBS-nst, pBBR3-SS) | present invention |
| DC7 | ZLKA (pBS-nst, pBBR3-SS) | present invention |
| DC7 | ZLKA (pBS-nst, pBBR3-SS) | present invention |
| DC0 | ZLKA (pBS-nst) | present invention |
| AZK1 | AZK (pBS-nst, pBBR3-SS) | present invention |
| NF3 | ZLKA (pUC-cstII, pBBR3-SS) | present invention |
| DC15 | ZLKA (pBS-cgtAII-nst, pBBR3-SS-wbpP, pSU-cgtB) | present invention |
| DC21 | ZLKA (pBS-cgtAII-nst, pBBR3-SS-gne, pSU-cgtB) | present invention |
| DC22 | ZLKA (pBS-cstIII-cgtAII, pBBR3-SS-gne, pSU-cgtB) | present invention |
| ZWT | ZLKA (pBS-nst, pBBR-SS-gne, pWKS-cgtAII) | present invention |
| ZWU2 | ZWU (pBS-nst, pBBR-SS-gne, pWKS-cgtAII) | present invention |
| NF08 | ZLKA (pUC18-cstII, pBBR3-SS-gne, pWKS-cgtAII) | present invention |

TABLE 1-continued

Genes, plasmids and *Escherichia coli* strains used in present invention

| | Description | Reference or source |
|---|---|---|
| NF09 | ZLKA (pUC18-cstII, pBBR3-SS-gne, pBAD33-cgtAII) | present invention |
| ZWU1 | ZWU (pUC18-cstII, pBBR3-SS-gne, pBAD33-cgtAII) | present invention |
| NF17 | ZLKA (pBS-cgtA-cstII, pSU-cgtB, pBBR-SS-gne) | present invention |
| GLK7 | GLKA (pBS-nst, pBBR3-SS) | present invention |
| SN4 | ZLKA (pBS-nst-nodC, pBBR3-SS, pWKS-lgtB-chiA) | present invention |
| NF21 | ZLKA (pBS-cstII-cgtB, pBBR3-SS-gne, pBAD33-cgtAII) | present invention |

DETAILED DESCRIPTION OF THE INVENTION

In a first embodiment, the invention relates to a method for producing oligosaccharides comprising at least one sialic acid residu, herein referred to sialylated oligosaccharides, the method comprising the step consisting of culturing a microorganism in a culture medium, optionally comprising an exogenous precursor, wherein said microorganism is capable of producing internally activated sialic acid and comprises heterologous genes encoding a CMP-Neu5Ac synthetase, a sialic acid synthase, a GlcNAc-6-phosphate 2 epimerase and a sialyltransferase, and wherein the endogenous genes coding for sialic acid aldolase (NanA) and for ManNac kinase (NanK) have been deleted or inactivated.

In the above method, and depending on the end-point, the heterologous sialyltransferase gene may be selected from α-2,3-Sialyltransferase, for example encoded by nst, α-2,3 α-2,8-Sialyltransferase (cstII), and α-2,3-Sialyltransferase (cstIII) or α-2,6-Sialyltransferase. The heterologous CMP-Neu5Ac synthetase may be neuA, the heterologous sialic acid synthase may be neuB, and the heterologous GlcNAc-6-phosphate 2 epimerase may be neuC. The neuA, neuB, and the neuC genes can be isolated from bacterial strains that contain sialylated structure in their cells envelope, such as *C. jejuni* strain ATCC Accession No. 43438.

The nanT, nanA, nanK and nanE genes are part of the same operon, which is regulated by the DNA binding protein NanR and induced by Neu5Ac (Kalivoda et al., 2003). Thus, the microorganisms of the invention can also be nanKEAT-. The production of Neu5Ac as intermediate during the synthesis of CMP-Neu5Ac by genetically engineered strain ovexpressing the neuBCA genes can thus induce the pathway of sialic acid catabolism and create two futile cycles that will reduce the capacity of CMP-Neu5Ac biosynthesis of the bacteria. A first futile cycle can result from the combined activity of the sialic acid synthase NeuB with the sialic acid aldolase NanA. A second futile cycle can result from the combined action of the UDP-GlcNAc 2 epimerase NeuC with the four enzymes NanK NanE NagA GlmM and GlmU that catalyse the formation of UDP-GlcNAc from ManNAc. According to the method proposed herein, degradation of Neu5Ac and ManNAc is prevented. This can be advantageously done by disrupting the nanA and nanK genes in the strains which will be used for sialylooligosaccharides production. In one specific embodiment, the nanT, nanA, nanK and nanE genes are deleted or inactivated. This can be practiced by removing the all operon for example.

In a preferred embodiment, the above microorganism encodes a protein that facilitates uptake of lactose and lacks enzymes that metabolize lactose. For example, in *E. coli*, the cell is preferably LacY+ (β-galactoside permease), LacZ− (β galactosidase), and optionally MelA− (α-galactosidase).

In another preferred embodiment, the medium comprises an exogenous precursor which is selected for example from lactose, galactose, β-galactoside, and α-galactoside, such as globotriose (Galα-4Galβ-4Glc).

The invention also relates to the above microorganism and to a cell culture medium comprising the above microorganism and an exogenous precursor selected from lactose, galactose, β-galactoside, and α-galactoside, such as globotriose (Galα-4Galβ-4Glc).

Definitions

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, Neu5Ac, or NANA). A second member of the family is N-glycolyl-neuraminic acid (Neu5Gc or NeuGc), in which the N-acetyl group of Neu5Ac is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$—$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

The term "bifunctional *Campylobacter jejuni* CstII sialyltransferase" refers to a sialyltransferase which exhibits both α-2,3 and α-2,8-Sialyltransferase activities. In some embodiments, the CstII sialyltransferase from ATCC Accession No. 43438 is used.

An "acceptor substrate" or an "acceptor saccharide" for a glycosyltransferase is an oligosaccharide moiety that can act as an acceptor for a particular glycosyltransferase. When the acceptor substrate is contacted with the corresponding glycosyltransferase and sugar donor substrate, and other necessary reaction mixture components, and the reaction mixture is incubated for a sufficient period of time, the glycosyltransferase transfers sugar residus from the sugar donor substrate to the acceptor substrate. For example, an acceptor substrate for the sialyltransferases used in the methods of the invention is lactose Galβ1,4-Glc.

A "donor substrate" for glycosyltransferases is an activated nucleotide sugar. Such activated sugars generally consist of uridine, guanosine, and cytidine monophosphate derivatives of the sugars (UMP, GMP and CMP, respectively) or diphosphate derivatives of the sugars (UDP, GDP and CDP, respectively) in which the nucleoside monophosphate or diphosphate serves as a leaving group. For example, a donor substrate for sialyltransferases used in the methods of the invention is CMP-Neu5Ac.

A "culture medium" refers to any liquid, semi-solid or solid media that can be used to support the growth of a microorganism used in the methods of the invention. In some embodiments, the microorganism is a bacteria, e.g., *E. coli*. Media for growing microorganisms are well known, see, e.g., Sambrook et al. and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel). Media can be rich media, e.g., Luria broth or terrific broth, or synthetic or semi-synthetic medium, e.g., M9 medium. In some preferred embodiments the growth medium comprises lactose and sialic acid.

"Commercial scale" refers to gram scale production of a sialylated product saccharide in a single reaction. In preferred embodiments, commercial scale refers to production of greater than about 50, 75, 80, 90 or 100, 125, 150, 175, or 200 grams.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

A "heterologous polynucleotide" or a "heterologous gene", as used herein, is one that originates from a source foreign to the particular host cell, or, if from the same source, is modified from its original form. Thus, a heterologous sialyltransferase gene in a cell includes a gene that is endogenous to the particular host cell but has been modified. Modification of the heterologous sequence may occur, e.g., by treating the DNA with a restriction enzyme to generate a DNA fragment that is capable of being operably linked to a promoter. Techniques such as site-directed mutagenesis are also useful for modifying a heterologous sequence.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used. Transcription termination signals, enhancers, and other nucleic acid sequences that influence gene expression, can also be included in an expression cassette. When more than one heterologous protein is expressed in a microorganism, the genes encoding the proteins can be expressed on a single expression cassette or on multiple expression cassettes that are compatible and can be maintained in the same cell. As used herein, expression cassette also encompasses nucleic acid constructs that are inserted into the chromosome of the host microorganism. Those of skill are aware that insertion of a nucleic acid into a chromosome can occur, e.g., by homologous recombination. An expression cassette can be constructed for production of more than one protein. The proteins can be regulated by a single promoter sequence, as for example, an operon. Or multiple proteins can be encoded by nucleic acids with individual promoters and ribosome binding sites.

The term "isolated" refers to material that is substantially or essentially free from components which interfere with the activity biological molecule. For cells, saccharides, nucleic acids, and polypeptides of the invention, the term "isolated" refers to material that is substantially or essentially free from components which normally accompany the material as found in its native state. Typically, isolated saccharides, oligosaccharides, proteins or nucleic acids of the invention are at least about 50%, 55%, 60%, 65%, 70%, 75%, 80% or 85% pure, usually at least about 90%, 91%, 92%, 93%, 94%, 95%, 96%, 97%, 98%, or 99% pure as measured by band intensity on a silver stained gel or other method for determining purity. Purity or homogeneity can be indicated by a number of means well known in the art, such as polyacrylamide gel electrophoresis of a protein or nucleic acid sample, followed by visualization upon staining. For certain purposes high resolution will be needed and HPLC or a similar means for purification utilized. For oligosaccharides, e.g., sialylated products, purity can be determined using, e.g., thin layer chromatography, HPLC, or mass spectroscopy.

The terms "identical" or percent "identity," in the context of two or more nucleic acid or polypeptide sequences, refer to two or more sequences or subsequences that are the same or have a specified percentage of amino acid residus or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80% or 85%, most preferably at least 90%, 91%, 92%, 93%, 94%, 95%, 96%, 97%, 98%, or 99% nucleotide or amino acid residu identity, when compared and aligned for maximum correspondence, as measured using one of the following sequence comparison algorithms or by visual inspection. Preferably, the substantial identity exists over a region of the sequences that is at least about 50 residus in length, more preferably over a region of at least about 100 residus, and most preferably the sequences are substantially identical over at least about 150 residus. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residus; always >0) and N (penalty score for mismatching residus; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residu alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques. In some embodiments, the nucleotide sequences that encode the enzymes are preferably optimized for expression in a particular Similarly, "conservative amino acid substitutions," in one or a few amino acids in an amino acid sequence are substituted with different amino acids with highly similar properties are also readily identified as being highly similar to a particular amino acid sequence, or to a particular nucleic acid sequence which encodes an amino acid. Such conservatively substituted variations of any particular sequence are a feature of the present invention. Individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. See, e.g., Creighton (1984) *Proteins,* W. H. Freeman and Company.

Bifunctional Sialyltransferases

As noted above, bifunctional sialyltransferases are used in the methods of the invention. Nucelic acids encoding such enzymes have been isolated from *C. jejuni* and are disclosed in U.S. Pat. Nos. 6,699,705 and 6,503,744 and WO/02074942. Exemplary *C. jejuni* strains which can be used as sources of bifunctional sialyltransferases include OH4384 (nucleic acid sequences are found in GenBank accessions AR271700 and AX934425), OH4382, O:10 (nucleic acid sequences are found in GenBank accessions AR271701 (SEQ ID No 1), AX934427 (SEQ ID No 2), O:23, and O:41 (nucleic acid sequences are found in GenBank accessions AR271702 (SEQ ID No 3) and AX934429 (SEQ ID No 4)). It shall be understood that conservatively modified variations as defined above of SEQ ID No 1, 2, 3 and 4 may be applied herein.

Host Cells

The recombinant cells of the invention are generally made by creating or otherwise obtaining a polynucleotide that encodes the particular enzyme(s) of interest, placing the polynucleotide in an expression cassette under the control of a promoter and other appropriate control signals, and introducing the expression cassette into a cell. More than one of the enzymes can be expressed in the same host cells using a variety of methods. For example, a single extrachromosomal vector can include multiple expression cassettes or more that one compatible extrachromosomal vector can be used maintain an expression cassette in a host cell. Expression cassettes can also be inserted into a host cell chromosome, using methods known to those of skill in the art. Those of skill will recognize that combinations of expression cassettes in extrachromosomal vectors and expression cassettes inserted into a host cell chromosome can also be used. Other modification of the host cell, described in detail below, can be performed to enhance production of the desired oligosaccharide. For example, the microorganism may be LacY+ allowing active transport of lactose. Host cells don't need to be NanT+ since activated sialylic acid is produced internally with the method according to the invention.

The recombinant cells of the invention are generally microorganisms, such as, for example, yeast cells, bacterial cells, or fungal cells. Examples of suitable cells include, for example, *Azotobacter* sp. (e.g., *A. vinelandii*), *Pseudomonas* sp., *Rhizobium* sp., *Erwinia* sp., *Bacillus* sp., *Streptomyces* sp., *Escherichia* sp. (e.g., *E. coli*), and *Klebsiella* sp., among many others. The cells can be of any of several genera, including *Saccharomyces* (e.g., *S. cerevisiae*), *Candida* (e.g., *C.* utilis, *C. parapsilosis, C. krusei, C. versatilis, C. lipolytica, C. zeylanoides, C. guilliermondii, C. albicans*, and *C. humicola*), *Pichia* (e.g., *P. farinosa* and *P. ohmeri*), *Torulopsis* (e.g., *T. candida, T. sphaerica, T. xylinus, T. famata*, and *T. versatilis*), *Debaryomyces* (e.g., *D. subglobosus, D. cantarellii, D. globosus, D. hansenii*, and *D. japonicus*), *Zygosaccharomyces* (e.g., *Z. rouxii* and *Z. bailii*), *Kluyveromyces* (e.g., *K marxianus*), *Hansenula* (e.g., *H. anomala* and *H. jadinii*), and *Brettanomyces* (e.g., *B. lambicus* and *B. anomalus*).

Promoters for use in *E. coli* include the T7, trp, or lambda promoters. A ribosome binding site and preferably a transcription termination signal are also provided. For expression of heterologous proteins in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*. Methods of transforming prokaryotes other than *E. coli* are well known. For example, methods of transforming Bacillus species and promoters that can be used to express proteins are taught in U.S. Pat. Nos. 6,255,076 and 6,770,475.

In yeast, convenient promoters include GAL1-10 (Johnson and Davies (1984) *Mol. Cell. Biol.* 4:1440-1448) ADH2 (Russell et al. (1983) *J. Biol. Chem.* 258:2674-2682), PHO5 (*EMBO J.* (1982) 6:675-680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al., *Gene* 61:265-275 (1987). For filamentous fungi such as, for example, strains of the fungi *Aspergillus* (McKnight et al., U.S. Pat. No. 4,935,349), examples of useful promoters include those derived from *Aspergillus nidulans* glycolytic genes, such as the ADH3 promoter (McKnight et al., *EMBO J.* 4: 2093 2099 (1985)) and the tpiA promoter. An example of a suitable terminator is the ADH3 terminator (McKnight et al.).

In some embodiments, the polynucleotides are placed under the control of an inducible promoter, which is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis. For *E. coli* and other bacterial host cells, inducible promoters are known to those of skill in the art. These include, for example, the lac promoter. A particularly preferred inducible promoter for expression in prokaryotes is a dual promoter that includes a tac promoter component linked to a promoter component obtained from a gene or genes that encode enzymes involved in galactose metabolism (e.g., a promoter from a UDPgalactose 4-epimerase gene (galE)).

Inducible promoters for other organisms are also well known to those of skill in the art. These include, for example, the arabinose promoter, the lacZ promoter, the metallothionein promoter, and the heat shock promoter, as well as many others.

The construction of polynucleotide constructs generally requires the use of vectors able to replicate in bacteria. A plethora of kits are commercially available for the purification of plasmids from bacteria. For their proper use, follow the manufacturer's instructions (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to construct the cells of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., *E. coli*, or other cells in which the vector is replicated prior to being introduced into the target cell. A number of selectable markers are known to those of skill in the art and are described for instance in Sambrook et al., supra. A preferred selectable marker for use in bacterial cells is a kanamycin resistance marker (Vieira and Messing, *Gene* 19: 259 (1982)). Use of kanamycin selection is advantageous over, for example, ampicillin selection because ampicillin is quickly degraded by β-lactamase in culture medium, thus removing selective pressure and allowing the culture to become overgrown with cells that do not contain the vector.

Construction of suitable vectors containing one or more of the above listed components employs standard ligation techniques as described in the references cited above. Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill.

A variety of common vectors suitable for constructing the recombinant cells of the invention are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2.

The methods for introducing the expression vectors into a chosen host cell are not particularly critical, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

PREFERRED EMBODIMENTS

Production of 3'Sialyllactose.

3'sialyllactose production can be carried out in a metabolically engineered strain defined above that expresses A gene coding for an enzyme comprising a α-2,3 sialyltransferase activity, such as a α-2,3 sialyltransferase or a bifunctional α-2,3 and α-2,8 sialyltransferase that use lactose as acceptor. As indicated, this strain is devoid of sialic acid aldolase, ManNAc kinase and β-Galactosidase activity and expresses heterologous genes encoding CMP-Neu5Ac synthetase, a sialic acid synthase, and a GlcNAc-6-phosphate 2 epimerase. For large scale production of sialyllactose, this strain can be cultivated at high cell density on inexpensive substrate such as glucose or glycerol and fed with lactose which will be internalized by the lactose permease and sialylated by the recombinant sialyltransferase using the CMP-Neu5Ac endogenously generated fom UDP-GlcNAc as shown in FIG. 1.

Production of 6'Sialyllactose

Here, the sialyltransferase gene is a gene encoding α-2,6 sialyltransferase such as the gene from *Photobacterium damsela* (Yamamoto et al., 1998) which results in the production of 6'sialyllactose (Neu5Acα-6Galβ-4Glc).

Production of GD3 and GT3 Sugar

GD3 (Neu5Acα-8Neu5Acα-3Galβ-4GlcCer) is a minor ganglioside found in most normal tissues in higher vertebrates including humans. The GD3 level has been shown to increase during some pathological situations, such as cancers (glioma, melanoma) and to have an important role in tumor angiogenesis Zeng, et al. *Cancer Res*, 60:6670 (2000). Thus, high scale and cost-effective production of GD3 is of particular interest. To reach this end-point, the heterologous sialyltransferase gene referred above is chosen from a gene encoding a bifunctional α-2,3 and α-2,8 sialyltransferase, for example such as the cstII gene from *Campylobacter jejuni* (Gilbert et al., 2002 and deposited under ATCC Accession No. 43438) and results in the production of GD3 and GT3 sugar. The bifunctional sialyltransferase polypeptide catalyzes the transfer of a sialyl moiety from an activated sialic acid molecule produced internally to the Neu5Acα-3Galβ-4Glc (GM3) to form Neu5Acα-8Neu5Acα-3Galβ-4Glc. This reaction may be further extended to produce GT3 which is the precursor of C series gangliosides which are the major constituents in adult fish brain and are found abundantly in fetal brains of higher vertebrates (Letinic, et al. *Neuroscience*, 86, 1 (1998)). They are also found in various neuroectodermal tumors and there is thus potentially great interest in having easy access to the GT3 oligosaccharide. To this end, the method herein further comprises culturing the microorganism such that the bifunctional *Campylobacter jejuni* sialyltransferase polypeptide catalyzes the transfer of a sialyl moiety from an activated sialic acid molecule produced internally to the Neu5Acα-8Neu5Acα-3Galβ-4Glc (GD3) to form Neu5Ac5α-8Neu5Acα-8Neu5Acα-3Galβ-4Glc (GT3).

Production of GM1 Sugar

Figure 2:
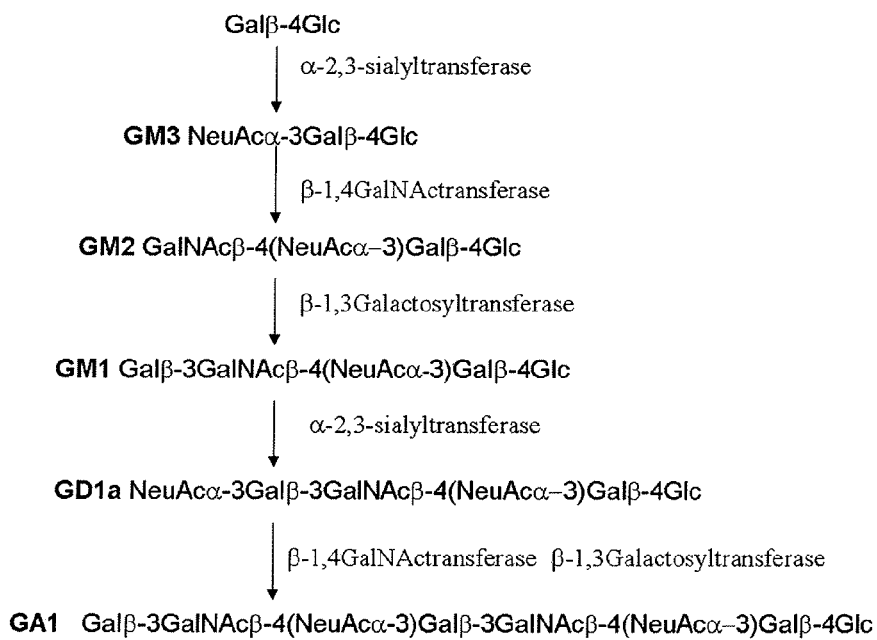
FIG. 2 shows the formation of side-products during production of GM1 sugar by metabolically engineered *E. coli* strains

As illustrated in FIG. 2, the system for sialyllactose production displayed above (see also FIG. 1) can be extended to the production of carbohydrate portion of the ganglioside GM1 by expressing the additional genes for a β-1,4GalNAc-transferase and for a β-1,3-Galactosyltransferase. Here, the microorganism of the invention is as displayed above in FIG. 1 and further comprises heterologous sequences encoding β-1,4GalNActransferase as well as β-1,3-Galactosyltransferase. In this embodiment, the β-1,4GalNActransferase transfers a UDP-GalNac residu to sialyllactose (GM3) to form GM2 and the β-1,3-galactosyltransferase transfers a Galactosyl residu to GM2 to form GM1. Strains may not be able to naturally produce UDP-GalNAc such as *E. coli* K12 strains. In this case, the strain of the invention can be complemented by a gene that encodes a UDP-GlcNAc 4 epimerase, such as for example the wbpP gene from *P. aeruginosa* (Creuzenet et al., 2000) and the gne gene from *C. jejuni* (Bernatchez et al., 2005). The GM1 sugar has a terminal non reducing galactose and this structure can be used as acceptor by α-2,3 sialyltransferase to produce the GD1a sugar. The GD1a sugar has the same terminal non reducing disaccharide structure than sialylactose and can be used as acceptor by the β-1,4GalNActransferase to form a heptasaccharide intermediate which can be galactosylated into the octasaccharide represented as GA1 (Galβ-3GalNAcβ-4(Neu5Acα-3)Galβ-3GalNAcβ-4(Neu5Acα-3)Galβ-4Glc) in FIG. 2.

The formation of the GD1a and its larger derivatives reduce the production yield of the GM1 sugar and it is one particular embodiment of the invention to reduce or abolish the formation of these side products. To this end, we discovered an α-2,3 sialyltransferase which is not able to use the GM1 sugar as acceptor. The *C. jejuni* strain NCTC 111168 expresses lipooligosaccharide structures that mimic the GM1 ganglioside (Linton et al., 2000). This lipooligosaccharide outer core structure was referred by Linton et al (2000) as the Outer core "VI". *C. jejuni* NCTC 111168 contains a gene called cstIII which encodes a protein showing a 53% sequence identity with sialyltransferase (CstII) from other *C. jejuni* strains that express GD1a mimic (Gilbert et al., 2002). The sialyltransferase activity of the CstIII protein allows advantageously the production of the GM1 sugar as the only oligosaccharide product. Thus, in one preferred embodiment, the invention contemplates the above method for the specific production of GM1, wherein the heterologous sialyl transferase is a α-2,3 sialyltransferase encoded by the cstIII gene isolated from the *C. jejuni* strains expressing lipooligosaccharide structures that mimic the GM1 ganglioside, such as the *C. jejuni* strain NCTC Accession No 111168.

Production of GM2 Sugar

Figure 3:
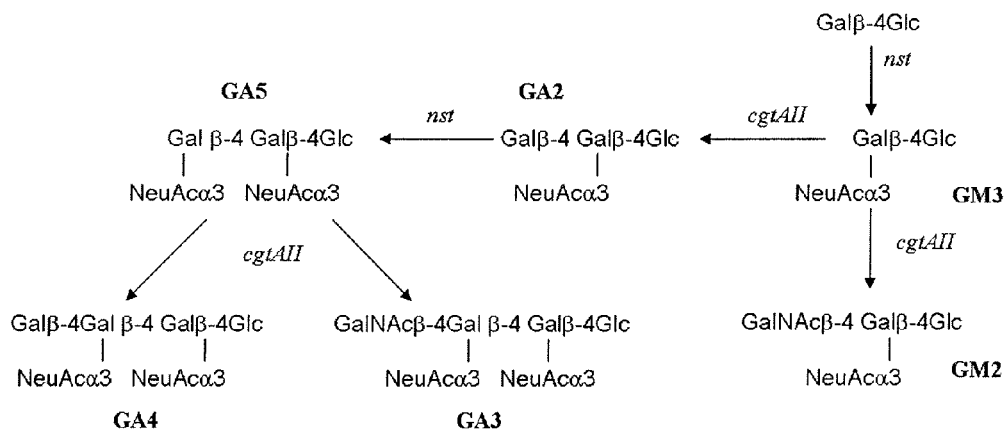
FIG. 3 shows the formation of side-products during biosynthesis of GM2 sugar

The system for sialyllactose production as described above can be extended to the production of carbohydrate portion of the ganglioside GM2 by expressing the additional genes for a β-1,4-GalNActransferase and for UDP-GlcNAc 4 epimerase. It has been previously reported that the CgtA β-1,4-GalNActransferase from *C. jejuni* exibits a β-1,4 Galactosyltransferase side activity which resulted in the production of the GM2 sugar analog designated as GA2 in FIG. 3 (Antoine et al., 2003). The GA2 sugar contains a terminal non reducing galactose and we have found that this galactose can served as acceptor for sialyltransferase to produce a disialylated tetrasaccharide (GA5, FIG. 3) which in turn can be converted into the pentasaccharide GA4 or GA3 (FIG. 3) by the very active CgtAII β-1,4-GalNActransferase.

Figure 4:
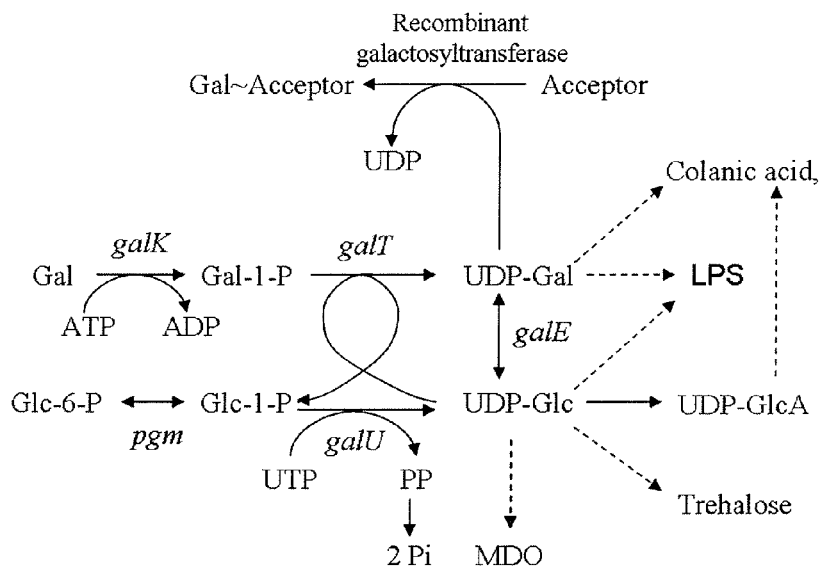
FIG. 4 shows the UDP-Gal biosynthetic pathway

The formation of the side products GA2, GA3, GA4 and GA5 reduces the GM2 sugar production yield and makes its purification more difficult. It is thus within the scope of the invention to abolish the formation of these side products. The β-1,4 Galactosyltransferase side activity can be advantageously suppressed by using mutant unable to produce UDP-Gal. As illustrated in FIG. 4, such mutant can be obtained by disrupting one of the three following genes: the galE gene encoding the UDP-glucose epimerase, the galU gene which encodes the UDP-Glc pyrophosphorylase, and the pgm gene that encodes the phosphoglucomutase. Thus, the invention is directed to a method as defined above for producing sialylated oligosaccharides, which is extended to the production of carbohydrate portion of the ganglioside GalNAcβ-4(Neu5Acα-3)Galβ-4Glc (GM2), wherein the microorganism further comprises heterologous sequences encoding a β-1,4-GalNActransferase, such as the CgtAII gene from *C. jejuni* O:36 strain ATCC Accession No 43456, and a UDP-GlcNAc 4 epimerase and wherein the micoorganism has at least one of the three following genes deleted or inactivated to disrupt the endogenous production of UDP-Gal: the galE gene encoding the UDP-glucose epimerase, the galU gene which encodes the UDP-Glc pyrophosphorylase, and the pgm gene which encodes the phosphoglucomutase, said disruption avoiding the production of side products such as GA2, GA3, GA4 and GA5.

Production of GD2 Sugar

The system for the production of GD3 sugar can be extended to the production of carbohydrate portion of the ganglioside GD2 by expressing the additional heterologous genes coding for a UDP-GlcNAc 4 epimerase and a β-1,4-GalNActransferase that use the GD3 sugar as acceptor, such as the CgtAII protein from *C. jejuni* O:36 strain ATCC Accession No 43456.

Figure 5:
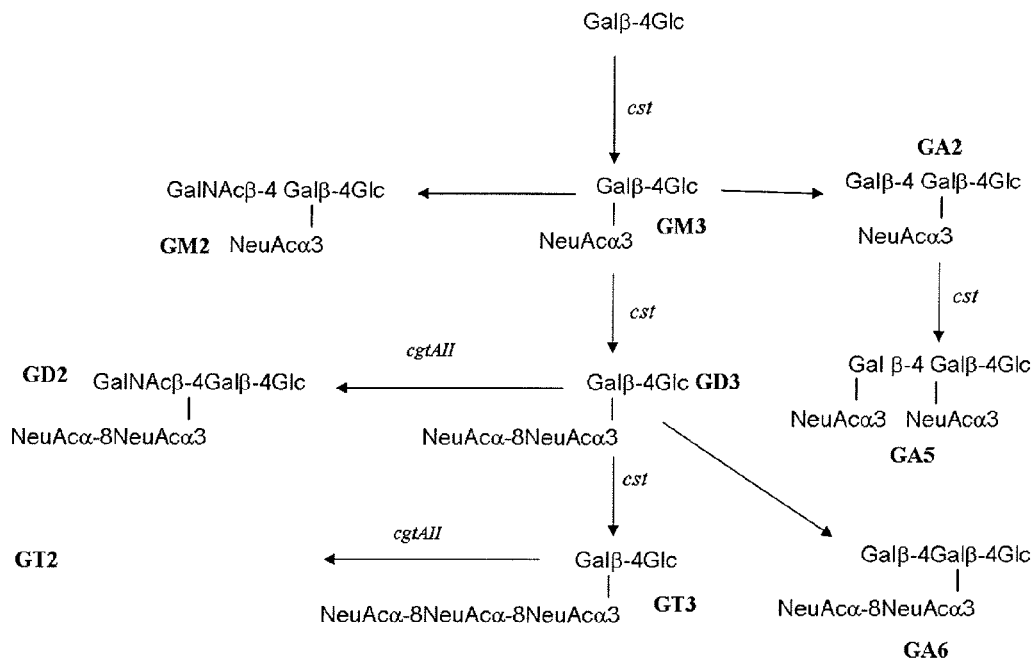
FIG. 5 shows the formation of side-products during biosynthesis of GD2 sugar

In this system, both the CstII sialyltransferase and the CgtAII GalNAc transferase compete for utilization of sialyllactose as acceptor (FIG. 5). To favour the production of GD2 sugar, we reduced the expression of cgtAII in the first phase of the culture (to allow sialyllactose to be mainly converted into GD3 sugar) and then increase the cgtAII expression in a second phase to convert GD3 into GD2. This can be done by placing the cgtAII gene under the control of a promotor which is regulated independently from the promotors that control the other genes. The β-1,4-Galactosyltransferase side activity of the CgtAII protein can result in the production of galactosylated analogs such as compounds GA2 GA5 and GA6 represented in FIG. 5. While these oligosaccharides may be of interest, it is also within the scope of the invention to prevent the formation of these side products by using mutant strain unable to produce UDP-Gal as depicted above for the GM2 production to lead to specific production of GD2.

Production of GD1b, GT1c, GT1b, GQ1b, GQ1c and GP1c Sugars

The production of GD1b sugar (Galβ-3GalNAcβ-4(Neu5Acα-8Neu5Acα-3)Galβ-4Glc) and GT1c sugar (Galβ-3GalNAcβ-4(Neu5Acα-8Neu5Acα-8Neu5Acα3)Galβ-4Glc) can be achieved by using the same combination of gene as in the GD2 sugar production system depicted above and by additionally expressing a β-3 Gal transferase gene. Here, the microorganism further comprises heterologous sequences encoding UDP-GlcNAc 4 epimerase, a β-1,4-GalNActransferase that use the GD3 and GT3 sugar as acceptor, such as the CgtAII protein from *C. jejuni* O:36 strain ATCC Accession No 43456. and a β-1,3-Galactosyltransferase, such as the cgtB gene from *C. jejuni* O:2 strain NCTC Accession No 11168.

The system for the production of GD1b and GT1c can be extended to the production of GT1b, GQ1c, GQ and GP1c by expressing a gene encoding a sialyltransferase that is able to use GD1b and GT1c as acceptor.

Production of GD1a and GT1a Sugars

Figure 6:
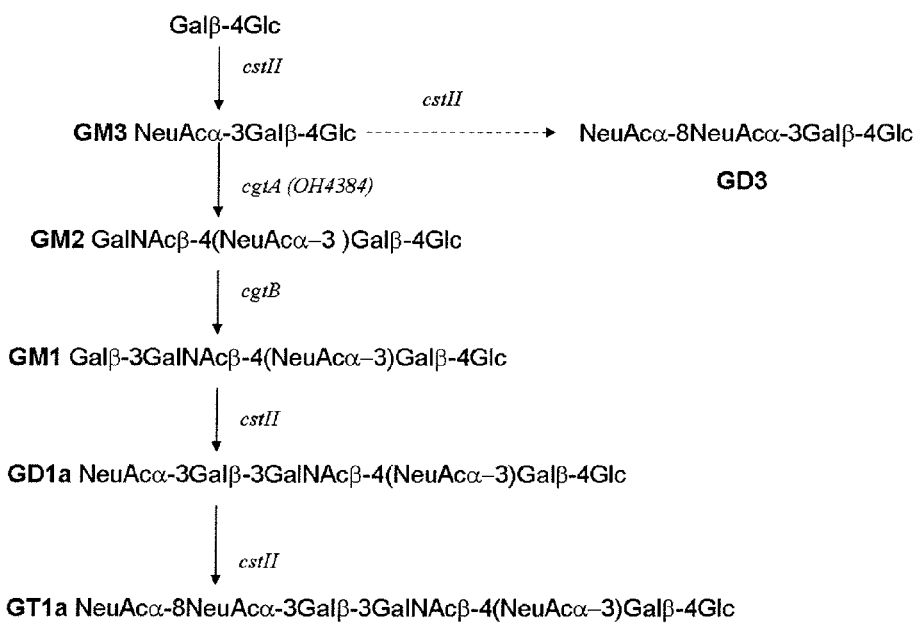
FIG. 6 shows the strategy for GT1a production using sialyltransferase

The strategy for the production of GT1a sugar is illustrated in FIG. 6 and relies on the coexpression of the cstII gene for the bifunctional sialyltransferase with the cgtA gene that encode a β-1,4GalNAc transferase which does not use GD3 sugar as acceptor, the end products being GD3, GD1a and GT1a sugars. Here, the invention relates to a method according as depicted above for producing sialylated oligosaccharides which is applied for producing specifically Neu5Acα-3Galβ-3GalNAcβ-4(Neu5Acα-3)Galβ-4Glc (GD1a) and Neu5Acα-8Neu5Acα-3Galβ-3GalNcβ-4(Neu5Acα-3) Galβ-4Glc (GT1a), wherein the microorganism comprises heterologous sequences coding for a bifunctional α-2,3 α-2,8-Sialyltransferase, such as the cstll gene from *C. jejuni* strain ATCC Acccession No 43438, a β-1,4-GalNAc transferase, such as the cgtAII gene from *C. jejuni* O:36 strain ATCC Accession No 43456, which does not use GD3 sugar as acceptor, and a β-3 Gal transferase, such as the cgtB gene from *C. jejuni* O:2 strain NCTC Accession No 11168.

Production of LST$_D$ (Sialyl-LNnT) and Sialyl-lewis X Oligosaccharides

Figure 7:
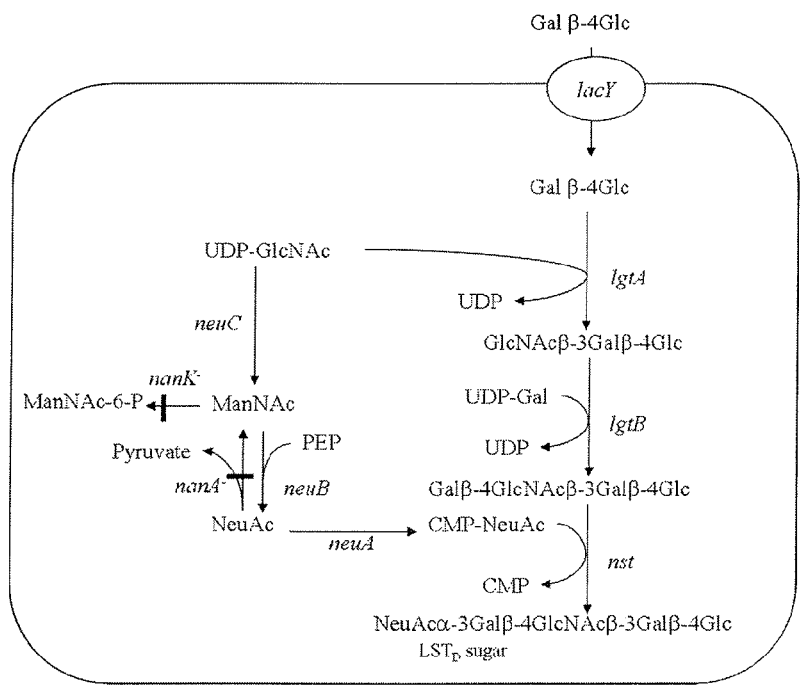
FIG. 7 shows the metabolically engineered pathway for the production of the $LST_D$ sugar (Neu5Acα-3Galβ-4GlcNacβ-3β-4Gal) from exogenous lactose

It has already been described that the tetrasaccharide LNnT (Galβ-4GlcNacβ-3Galβ-4Glc) can be produced from exogenous lactose by metabolically engineered strain expressing the lgtA and lgtB gene encoding β-1,3 GlcNAc transferase and β-1,4Galactosyltransferase respectively (Priem et al., 2002). The above system for producing sialylated oligosaccharides can be extended to the production of the pentasaccharide LST$_D$ (Neu5Acα-3Galβ-4GlcNacβ-3Galβ-4Glc) by expressing the additional gene nst and neuBCA in a nanK–, nanA– strain as illustrated in FIG. 7. The system for the synthesis of LST$_D$ can be combined with the fucosylation system that we have described for the production of Lewis X oligosaccharide (Dumon et al., 2004) to produce oligosaccharides carrying the sialyl-lewis X motif (Neu5Acα-3Galβ-4(Fucα-3)GlcNacβ-) at their non reducing end. In this regard, the micro organism further comprises a heterologous sequence coding for a α-1,3-fucosyltransferase such as the *Helicobacter pylori* futA (for example SEQ ID No 18—from *Helicobacter pylori* ATCC Accession No 26695) and futB (for example SEQ ID No 19—from *Helicobacter pylori* ATCC Accession No 26695).

Production of Sialosyl Galactosyl Globoside (SGG) Hexasaccharide

The sialosyl galactosyl globoside (Neu5Acα-3Galβ-3GalNAcβ-3Galα-4Galβ-4Gal) has been found to be the preferred binding receptor for uropathogenic *Escherichia coli* (Stapleton et al., 1998) and could potentially be used as an anti-infective agent. The production of the SGG hexasaccharide from globotriose has recently been described using exogenously added sialic acid (Efficient production of globosides sugar using metabolically engineered microorganisms in our U.S. Patent application U.S. 60/711,406). The production of SGG hexasaccharide was carried out by a nanA– melA– strain expressing (i) the *Haemophilus influenzae* (strain rd) lgtD gene that encoded both a GalNAc transferase and a Galactosyltransferase activities, (ii) the nst sialyltransferase (α-2,3 sialyltransferase, such as for example from *N. meningitidis*, such the MC58 strain: GenBanK accession number U60660—SEQ ID No 5, protein_id=AAC44541.1—SEQ ID No 6) which catalyzes the transfer of a sialyl moiety from an activated sialic acid molecule to globopentaose to form sialosyl galactosyl globoside (SGG) hexasaccharide, (iii) the neuA gene for CMP Neu5Ac synthase and (iv) the wbpP gene for UDP-GlcNAc epimerase.

Figure 8:
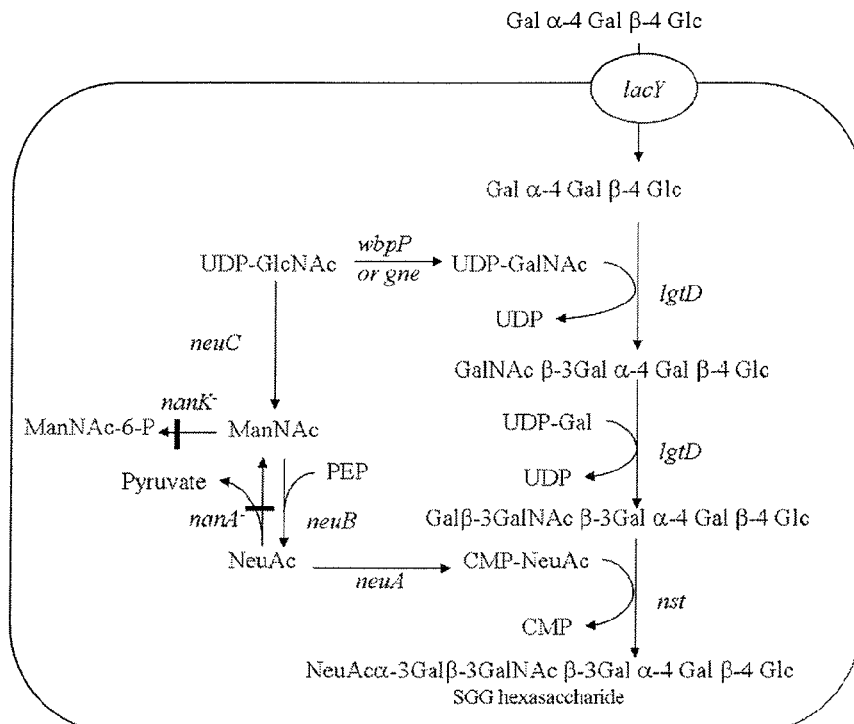
FIG. 8 shows the metabolically engineered pathway for the production of the SGG hexasaccharide (Neu5Acα-3Galβ-3GalNacβ-3Galα-4Galβ-4Gal) from exogenous globotriose.

This system has been modified to work without sialic acid addition by using a nanK– nanA– melA– strain and by additionally expressing the neuABC genes as illustrated in FIG. 8.

In some embodiments, the microorganisms are manipulated to enhance transport of an acceptor saccharide into the cell. Here, where lactose or globotriose is the acceptor saccharide, *E. coli* cells that express or overexpress the LacY permease can be used.

Thus, the invention embraces the above method wherein the microorganism is cultured in a medium with globotriose and is LacY+, MelA–, nanT+, nanA⁻, nanK– and comprises heterologous lgtD, genes for α-2,3-Sialyltransferase and UGP-GlcNAc C4 epimerase as well as the neuABC genes.

The invention also provides a coupling method in which a first microorganism is used to prepare globosides. As mentioned above, the culture medium may include lactose or globotriose but there is no need to supply sialic acid in the configuration herein since it is produced internally. When globotriose is used, the invention also contemplates a set of two separate micoorganisms, the said first microorganism being cultured in a medium with lactose and being LacY+, LacZ–, MelA– and comprising a heterologous lgtC gene to produce globotriose (α-1,4-Gal transferase enzyme can be encoded for example by LgtC genes of *N. meningitidis*, *N. gonorrhoeae* or *Haemophilus influenzae*, more particularly by the LgtC gene of *Neisseria meningititis* L1 (126E) GenBank accession number U65788—SEQ ID NO:7, protein_id AAB48385—SEQ ID NO:8); the second microorganism being cultured in a medium with globotriose and being LacY+, MelA+, nanT+, nanA.sup.-, nanK– and comprising heterologous lgtD, wbpP and nst genes as well as the neuABC genes. The gene lgtD encodes a β-3GalNAc transferase to catalyze the transfer of a galactose moiety from UDP-Gal to globotetraose to form globopentaose (β-3 Gal transferase activity). For example, the lgtD gene from *Haemophilus influenzae* HI1578, GenBanK accession number U32832—SEQ ID NO:9, protein_id=AAC23227—SEQ ID NO:10 can be used.

Production of Sialylgalactose

It has recently been shown that galK mutant lacking galactokinase activity can use exogenous galactose as acceptor for the synthesis of olihosaccharides with a terminal reducing galactose (Dumon et al., 2005). The method for producing sialylated oligosaccharides as described above can be advantageously used to produce the disaccharide sialylgalactose (Neu5Acα-3Gal) by a microorganism galK–, nanA– and nanK– (or nanKEAT-) expressing the gene for sialyltransferase and the neuBCA genes cultured in a medium with galactose.

Production of Sialylated Oligosaccharides with a Terminal Reducing Galactose

The method for the synthesis of sialygalactose can be adapted to the production of analogs of all the sialylated structure mentioned above. The use of galactose as acceptor in place of lactose result in the formation of analogs lacking the terminal glucose residu.

Production of Sialylated Oligosaccharides with a Terminal Lactose or Galactose Carrying Latent Chemical Functions The broad specificity of the sugar permease can be used to internalize lactose or galactose derivatives carrying latent chemical functions to produce conjugatable oligosaccharides. This strategy has been successfully applied to the synthesis of the oligosaccharide portions of GM2 and GM3 gangliosides with an allyl or a propargyl aglycon (Fort et al., 2005). The alkyne function makes possible an azido addition under aqueous conditions and the alkene function can either be converted into an aldehyde to be linked to proteins by reductive amination, or be transformed into a versatile amino group by the addition of cysteamine. Other chemical function such as azide or amine group can also be used. All these lactose or galactose derivatives can be advantageously used to produce conjugatable analogs of all the sialylated structure mentioned above.

Production of Sialylated Oligosaccharides with Chitooligosaccharide Structure at their Reducing End

*E. coli* strains overexpressing the *Azorhizobium caulinodans* nodC gene for chitin-oligosaccharide synthase have been shown to produce more than 2 g.l$^{-1}$ of chitinpentaose when they were cultivated at high cell density (Samain et al., 1997). Once produced in the cytoplasm, chitinpentaose can serve as acceptor for glycosyltransferases that recognize a terminal non-reducing GlcNAc residu. This strategy was used for the synthesis of the hexasaccharide Galβ-4[GlcNAcβ-4]$_4$GlcNAc by an *E. coli* strain that co-expressed the *Azorhizobium caulinodans* nodC gene and the *Neisseria meningitidis* lgtB gene for β-1,4-Galactosyltransferase (Bettler et al., 1999). The terminal N-acetyllactosamine motif of this hexasaccharide is an acceptor for sialyltransferase. The sialylated heptasaccharide Neu5Acα-3Galβ-4[GlcNAcβ-4]$_4$GlcNAc can thus be advantageously produced in nanK, nanA mutant strains coexpressing nodC, lgtB, nst and neuBCA. A recently developed strategy to reduce this size is to enzymatically hydrolyze the chitinpentaose by a chitinase in the living bacteria as soon as it is produced by NodC (Cottaz & Samain, 2005). We have found that it is possible within the method of the invention to avoid formation of large size chitinpentaose primer, which considerably increases the molecular weight of the target structures using the chitinase gene from *Bacillus circulans* for example.

Figure 9:
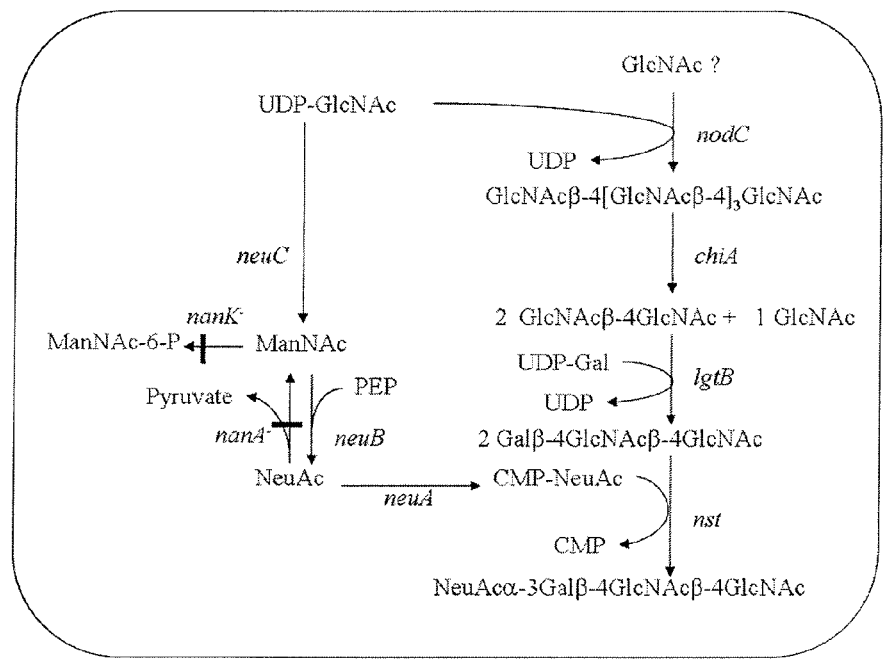
FIG. 9 shows the metabolically engineered pathway for the production of the sialylated tetrasaccharide (Neu5Acα-3Galβ-4GlcNacβ-4GlcNAc).

As illustrated in FIG. 9, the method of the invention enable the formation of the sialylated tetrasaccharide Neu5Acα-3Galβ-4GlcNAcβ-4GlcNAc by nanK–, nanA– strains coexpressing nodC, chiA, lgtB, nst and neuBCA. Thus, the invention relates to the above method; or alternatively a method wherein no exogenous is added to the culture medium; for producing sialylated oligosaccharides with chitooligosaccharide structure at their reducing end, such as the sialylated heptasaccharide Neu5Acα-3Galβ-4[GlcNAcβ-4]$_4$GlcNAc, wherein the sialyl-transferase is a α-2,3-Sialyltransferase, such as the *Neisseria* nst gene, and the microorganism further comprises a chitin oligosaccharide synthase such as the *Azorhizobium caulinodans* nodC gene and a β-1,4-Galactosyltransferase gene such as the *Neisseria meningitidis* lgtB gene. It can be extended to the production of sialylated tetrasaccharide Neu5Acα-3Galβ-4GlcNAcβ-4GlcNAc, wherein the microorganism further comprises a heterologous sequence encoding a chitinase, such as the chiA gene.

In still another aspect, the invention is directed to a micoorganism as defined avove as well as to a cell culture medium comprising an exogenous precursor selected from lactose, galactose, β-galactoside, and α-galactoside such as globotriose (Galα-4Galβ-4Glc) and said microorganism.

EXAMPLE 1

Construction of nanA, nanKA and nanKETA Mutants

All mutants were constructed from strain DC (Dumon et al., 2005) which was a strain DH1 derivative carrying the lacZ and lacA mutations. Since all derivatives of strain DH1 are recA mutant, they were transformed with the low copy plasmid pEXT22 (Dykxhoorn et al., 1996) carrying a functional recA gene and a kanamycin resistance to recover a transient RecA$^+$ phenotype for the gene inactivation procedure that involved DNA recombination. Once the gene has been disrupted, the plasmid was cured by growing the cell without kanamycin and screening for RecA$^-$ phenotype.

The strain AZL was constructed from strain DC by inactivating nanA using the suicide plasmid pMAK705 (Hamilton et al., 1989) as previously described (Priem et al., 2002).

To construct the strain ZLKA from strain DC, the nanKETA genes were disrupted by removing a 3.339 kb segment in the chromosomal DNA using the previously described one-step procedure that employs PCR primers to provide the homology to the targeted sequence (Datsenko & Wanner, 2000). The sequence of the upstream primer was 5'GCAATTATTGATTCGGCGGATGGTTTGCCGATG-GTGGTGTAGGCTGGAGCTGCTT C (SEQ ID No 11) and the sequence of the downstream primer was 5' CTCGTCAC-CCTGCCCGGCGCGCGTGAAAAT-AGTTTTCGCATATGAATATCCTCCTT AG. ((SEQ ID No 12).

The same procedure was used to inactivate the nanK gene in strain AZL to obtain the strain AZK except that the size of the deleted fragment was 0.537 kb and that the sequence of the upstream primer was (SEQ ID No 13)
5' CACTGGCGATTGATATCGGCGGTACTAAACTTGCCGCCGTGTAGGC

TGGAGCTGCTTC.

EXAMPLE 2

Cloning of neuBCA Genes

A 2.995 DNA fragment containing the sequence of the genes neuBCA was amplified by PCR using the genomic DNA of *Campylobacter jejuni* strain ATCC 43438 as a template.
A KpnI site was added to the left primer:

```
                                      (SEQ ID No 14)
5'GGTACCTAAGGAGGAAAATAAATGAAAGAAATAAAAATACAA
``` and a XhoI site was added to the right primer

```
                                      (SEQ ID No 15)
5'CTCGAGTTAAGTCTCTAATCGATTGTTTTCCAATG.
```

The amplified fragment was first cloned into pCR4Blunt-TOPO vector (Invitrogen) and then sub-cloned into the KpnI and XhoI sites of pBBR1-MCS3 vector to form pBBR3-SS.

EXAMPLE 3

Production of Sialyllactose by Metabolically Engineered E. coli Strains

Sialyllactose production was investigated with different mutant strains contained the *N. meningitidis* nst gene for α-2,3 sialyltranferase and the pBBR3-SS plasmid that contained the *C. jejuni* genes neuC, neuB and neuA encoding N-acetylglucosamine-6-phosphate-epimerase, sialic acid synthase and CMP-Neu5Ac synthetase respectively. Production of sialyllactose was estimated by the colorimetric quantification of sialic acid in both the intra and extracellular fractions (Table 2). The results showed that the nanA mutant AW1 and the DC6 strain, which contained no mutation in the sialic acid operon, produced low amount of sialyllactose with a similar production yield. The two mutants AZK1 and DC7 that carried the nanK and nanA mutations both produce a four time higher quantities of sialyllactose. No sialic acid could be detected in the control culture of DC7 incubated without lactose, indicating the high level of total sialic acid corresponded to the formation of sialyllactose.

Improvement of sialyllactose production was also confirmed by TLC analysis which showed that the band corresponding to sialyllactose was much more intense in DC7 and AZK1 extracts that in DC6 and AW1 extracts.

Total sialic acid was quantified by the diphenylamine method (Werner & Odin, 1952). Cultures were incubated 30 hours after addition of Lactose was supplied at a concentration of 7.5 g/l except for the control culture of DC7 without lactose.

EXAMPLE 4

Large Scale Production of Sialyllactose with Continuous Feeding of Lactose

Figure 10:
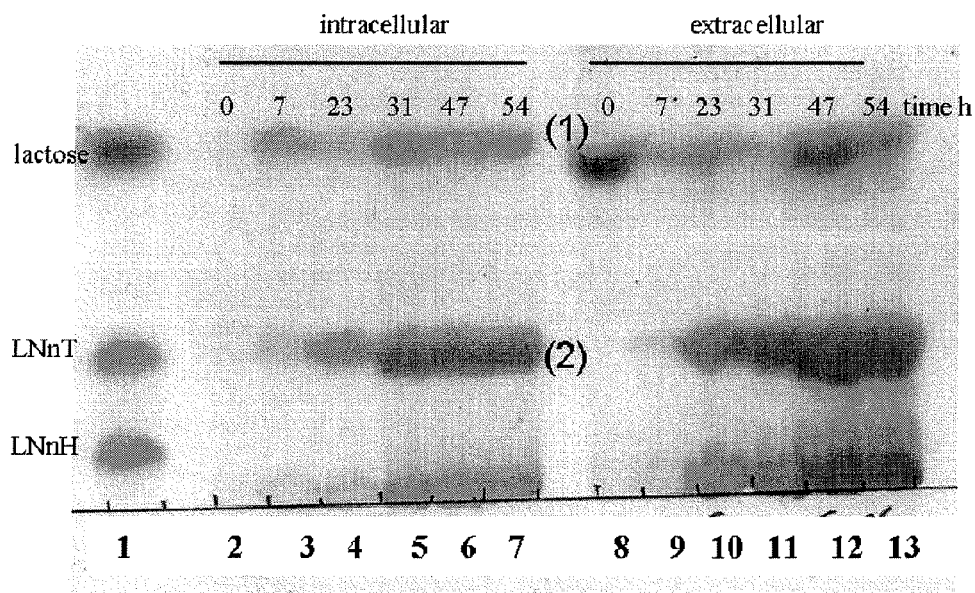
FIG. 10 is a TLC analysis of intracellular and extracellular fraction of high cell density culture of strain DC7 with a continous feeding of lactose. Lanes 1: standard solution (2 mg.ml$^{-1}$ each) of lactose, lacto-N-neotraose (LNnT), lacto-N-neohexaose (LNnH). Lanes 2, 3, 4, 5, 6 and 7: intracellular fractions withdrawn 0, 7, 23, 31, 47 and 54 hours after lactose addition. Lanes 8, 9, 10, 11, 12 and 13: extracellular fractions withdrawn 0, 7, 23, 31, 47 and 54 hours after lactose addition. Sialyllactose (2) has been previously shown to migrate as the tetrasaccharide LNnT.

This production yield was increased by extending the cultivation time to 71 hours. Lactose was added at a concentration of 2 g.l$^{-1}$ at the beginning of the fed-batch phases. It was first added continuously with an input rate of 0.52 g.l$^{-1}$.h$^{-1}$ for 5 hours in the phase with a high glycerol feeding rate. The lactose input rate was then decrease to 0.3 g.l$^{-1}$.h$^{-1}$ until the end of the culture in the second phase with a low glycerol feeding rate. TLC analysis showed that sialyllactose (compound 2, FIG. 10) was continuously produced until the end of the culture and that sialyllactose production was not limited by the supply of lactose (compound 1) which could always be detected in small amount throughout the culture in the intracellular fraction.

Figure 11:
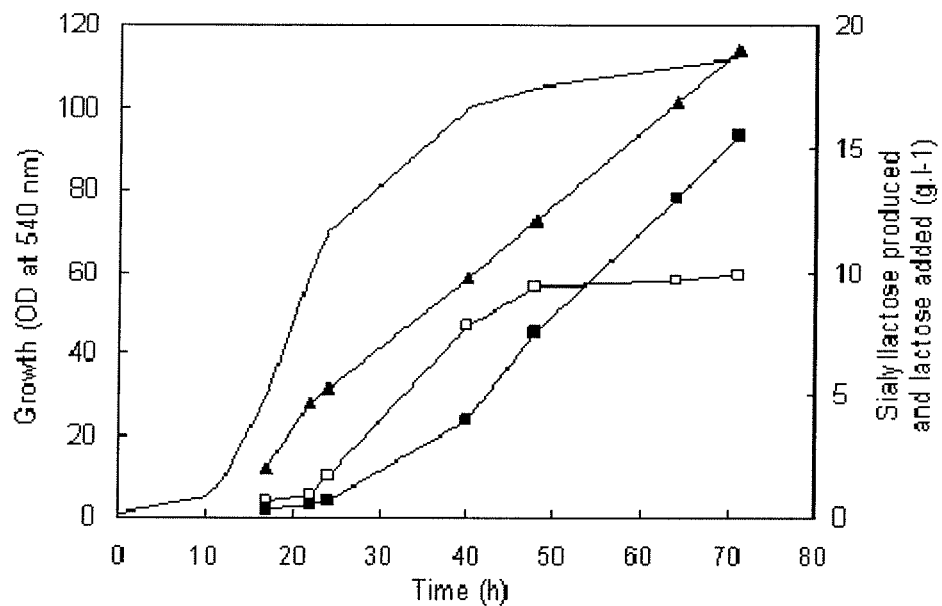
FIG. 11 shows the production of sialyllactose in high cell density culture of strain DC7 with a continous feeding of lactose. (▲) cumulated amount of added lactose, (□) intracellular sialyllactose, (■) extracellular sailayllactose, (–) bacterial growth.

Colorimetric quantification of sialic acid indicated that sialyllactose accumulated mainly in the intracellular fraction in the first part of the culture. The intracellular sialyllactose concentration then plateaued at around 10 g.l$^{-1}$ and the sialyllactose, which was additionally produced, was then secreted in the extracellular medium where it accumulated at a final concentration of 15.5 g.l$^{-1}$ (FIG. 11).

EXAMPLE 5

Purification of Sialyllactose

Sialyllactose was purified from one liter of DC7 culture obtained as described in example 4. At the end of the culture, the extracellular fraction was separated from the cells by centrifugation. The pH of the extracellular fraction was lowered to 3.00 by the addition of a strong cation exchanger resin (Amberlite IR120 H$^+$ form). This resulted in the precipitation of proteins which were removed by centrifugation. The pH of the clear supernatant was then adjusted to 6.0 by the addition of a week anion exchanger (Dowex 66 free base form) and half of the supernatant was then loaded on a Dowex 1 (HCO3 form) column (5×20 cm). Sialyllactose was retained by Dowex 1 resin and, after washing with distilled water, was eluted with a 0-500 mM continuous NaHCO3 gradient. The

TABLE 2

Colorimetric quantification of sialic acid in intracellular and extracellular fractions of high cell density cultures of strains genetically engineered for the production of sialyllactose

| Strain | mutation | hetrologous genes expressed | accepteur | Neu5Ac concentration (g · l−1) intracellular | extracellular |
|---|---|---|---|---|---|
| DC | | none | lactose | 0 | 0 |
| DC6 | | neuBCA nst | lactose | 0.94 | 0.43 |
| AW1 | nanA | neuBCA nst | lactose | 1.13 | 0.27 |
| DC7 | nanKETA | neuBCA nst | lactose | 2.32 | 3.25 |
| DC7 | nanKETA | neuBCA nst | none | 0.11 | 0 |
| DC0 | nanKETA | neuBCA | lactose | 0 | 0 |
| AZK1 | nanK nanA | neuBCA nst | lactose | 2.16 | 2.93 | same procedure was repeated with the other half of the supernatant. Eluted fractions containing sialyllactose were pooled and the NaHCO3 was removed by a treatment with Amberlite IR120 ($H^+$ form) until pH 3.0. The pH was the adjusted to 6.0 with NaOH and the sialyllactose was freeze-dried.

For the purification of the intracellular fraction, the cells were permeabilized by heating (100° C., 45 min) and resuspended in the same volume as the initial culture medium.

Oligosaccharides freely diffused outside of the cells and were recovered in the supernatant after centrifugation. The purification of sialyllactose was then carried out using the same protocol as for the extracellular fraction.

From a one liter culture of strain DC7, the yield of purified sialyllactose was 9 grams from the extracellular fraction and 6 grams from the intracellular fraction. Identification of the purified product as sialyllactose was confirmed by mass spectrometry analysis.

EXAMPLE 6

Production of GD3 and GT3 Sugars

Figure 12:
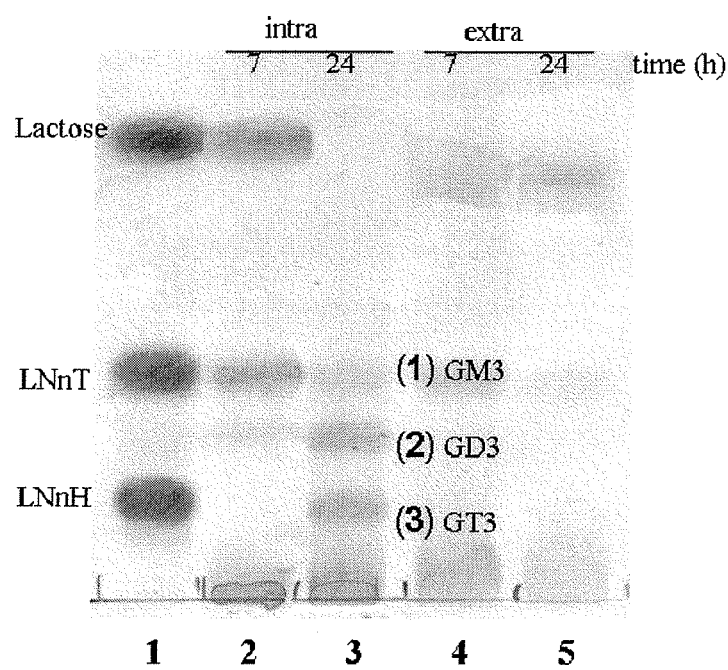
FIG. 12 is a TLC analysis of oligosaccharides produced by high cell density culture of strain NF03 containing the plasmids pUC18-cstII and pBBR3-SS. The initial lactose concentration was 3 g.l$^{-1}$. Lanes 1: standard solution (2 mg.ml$^{-1}$ each) of lactose lacto-N-neotetraose (LNnT), lacto-N-neohexaose (LNnH). Lanes 2 and 3: intracellular fractions withdrawn 7 and 24 hours after lactose addition. Lanes 4 and 5: extracellular fractions withdrawn 7 and 24 hours after lactose addition.

The production of the GD3 and GT3 sugars from exogenous lactose and Neu5Ac has been previously described using metabolically engineered strain expressing the cstII *Campylobacter jejuni* gene for the bifunctional α-2,3 and α-2,8 sialyltransferase (Antoine et al., 2005). Here we have investigated the production of these two oligosaccharides without exogenous supply of sialic acid by using the system described in example 3. The GD3 producing strain NF3 was a nanKEAT mutant which co-expressed cstII and neuBCA (Table I). The strain NF3 was cultivated at high cell density in presence of 3 $g.l^{-1}$ of lactose. The TLC analysis (FIG. 12) showed that lactose was entirely converted into three compounds which were presumed to be GM3 (1) GD3 (2) and GT3 (3) sugars.

The intracellular fraction from strain NF03 culture was purified by ion exchange chromatography on Dowex 1 as described in example 4 and three oligosaccharide fractions containing the GM3, GD3, and GT3 sugars respectively were separated. The yields of the three sugar fractions were 0.16 g, 0.75 g and 1.26 g respectively. Identification was confirmed by mass spectrometry analysis of the purified fractions.

EXAMPLE 7

Production of GM1 Sugar Using the *N. meningitidis* Sialyltransferase and the *P. aeruginosa* UDP-GlcNAc C4 Epimerase The production of the GM1 sugar from exogenous lactose and Neu5Ac has been previously described using a metabolically engineered strain expressing: (i) the *N. meningitidis* nst gene for α-2,3-Sialyltranferase; (ii) the cgtA gene from *C. jejuni* O:19 strain OH4384, which encodes a β-1,4-GalNAc transferase; (iii) the cgtB gene from *Campylobacter jejuni* strain NCTC 11168, which encode β-1,4-Galactosyltransferase, (iv) the wbpP gene from *P. aeruginosa* which encodes a UDP-GlcNAc C4 epimerase (Antoine et al., 2003). First attempts to produce GM1 sugar without exogenous addition of sialic acid by coexpressing cgtA, cgtB and nst with neuBCA indicated that the limiting step was the conversion of sialyllactose into GM2 sugar by the CgtA GalNAc transferase. The GalNAc transferases have been shown to exist in different version depending on the *Campylobacter* strains. The cgtA version cloned from strain OH4384 was reported to have a specific activity largely lower than those of versions from strain ATCC 4356 or NTCC 11168 (Gilbert et al., 2002; Varki, 1993). The cgtAII gene was thus cloned by PCR from the genomic DNA of strain ATCC 4356 and subcloned with the nst gene into a pBluescript plasmid, yielding to the pBS-cgtAII-nst plasmid (Table I). The wbpP gene was cloned from the pBBRwbpP plasmid (Antoine et al., 2003) downstream the neuBCA gene in pBBR3-SS, yielding to pBBR-SS-wbpP. The cgtB was cloned from the pACT3cgtAB plasmid (Antoine et al., 2003) into the pSU27-18 plasmid, yielding to pSU18-cgtB. The DC15 strain was constructed by transforming the nanKEAT mutant strain ZLKA with the three plasmids pBS-cgtAII-nst, pBBR-SS-wbpP and pSU18-cgtB (table 1).

Figure 13:
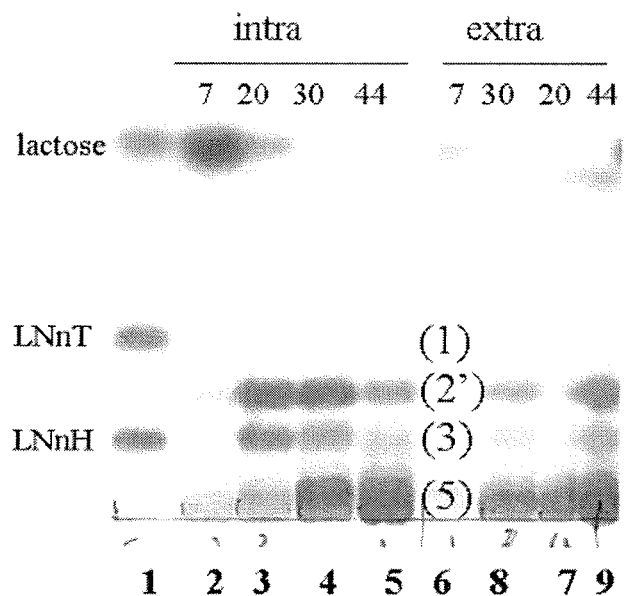
FIG. 13 is a TLC analysis of oligosaccharides produced by high cell density culture of strain DC15 (pBS-cgtAII-nst, pBBR3-SS-wbpP, pSU-cgtB). The initial lactose concentration was 5 g.l$^{-1}$. Lanes 1: standard solution (2 mg.ml$^{-1}$ each) of lactose lacto-N-neotetraose (LNnT), lacto-N-neohexaose (LNnH). Lanes 2, 3, 4, 5: intracellular fractions withdrawn 7, 20, 30 and 44 hours after lactose addition. Lanes 6, 7, 8, 9: extracellular fractions withdrawn 7, 20, 30 and 44 hours after lactose addition. Sialyllactose (1) and the GM1 sugar (3) migrate as LNnT and LNnH respectively.

As shown in FIG. 13, the strain DC15 did not accumulate the GM3 sugar (1), indicating that the CgtAII from strain ATCC 4356 was considerably more active than CgtA from strain 0144384. At the end of the culture, the major products were a compound (5) which migrated slower than the GM1 sugar and a compound (2') that migrated as the GM2 sugar. After purification on Dowex1, the mass spectrometry analysis indicated that compound (2') was a GM2 sugar analog which has a Gal residue in place of GalNAc and which was further designated as GA2 sugar (Table 3). Structure was: Galβ-4(Neu5Acα-3)Galβ-4Glc The mass spectrum of compound (5) suggest it was a disialylated octasaccharide formed by the transfert of two sugar residue (one HexNAc and one Hex) on the GD1a sugar. Since these two sugars being most probably added by CgtAII and CgtB, the structure of compound (5), which was further designated as GA1 sugar, is likely to be: Galβ-3GalNAcβ-4Neu5Acα-3Galβ-3GalNAcβ-4(Neu5Acα.-3)Galβ-4Glc (Table 3).

TABLE 3

Structure of ganglioside sugar analogs formed as side-products during the syntheseis of ganglioside sugar in reason of the β-1,4Galactosyltransferase activity of the CgtA β-1,4-GalNActransferase.

| Structure | name in the text |
|---|---|
| Galβ-3GalNAcβ-4(Neu5Acα-3)Galβ-3GalNAcβ-4(Neu5Acα-3)Galβ-4Glc | GA1 |
| Galβ-4(Neu5Acα-3)Galβ4Glc | GA2 |
| GalNAcβ-4(Neu5Acα-3)Galβ-4(Neu5Acα-3)Galβ-4Glc | GA3 |
| Galβ-4(Neu5Acα-3)Galβ-4(Neu5Acα-3)Galβ-4Glc | GA4 |
| Neu5Acα-3Galβ-4(Neu5Acα-3)Galβ-4Glc | GA5 |
| Galβ-4(Neu5Acα-8Neu5Acα-3)Galβ-4Glc | GA6 |

EXAMPLE 8

Production of GM1 Sugar Using the *N. meningitidis* Sialyltransferase and the *Campylobacter* UDP-Gal C4 Epimerase (GNE)

The GA2 sugar was produced by culture DC15 because the CgtAII is extremely active and can use UDP-Gal as a sugar donor instead of UDP-GalNAc in case of a shortage of UDP-GalNAc. Since this shortage can be due to an insufficient activity of the UDP-GlcNAc C4 epimerase encoded by wbpP, the utilisation of the epimerase encoded by the *C. jejuni* gne gene was investigated. This gene has recently been shown to be more active than WbpP (Bernatchez et al., 2005). The gne gene was cloned by PCR from the genomic DNA of *C. jejuni* strain NCTC 111168 and subcloned in plasmid pBBR-SS downstream the neuBCA genes. The resulting plasmid pBBR-SS-gne was used to construct the strain DC21 which was similar to strain DC 15 except that it expressed gne instead of wbpP. (Table 1).

Figure 14:
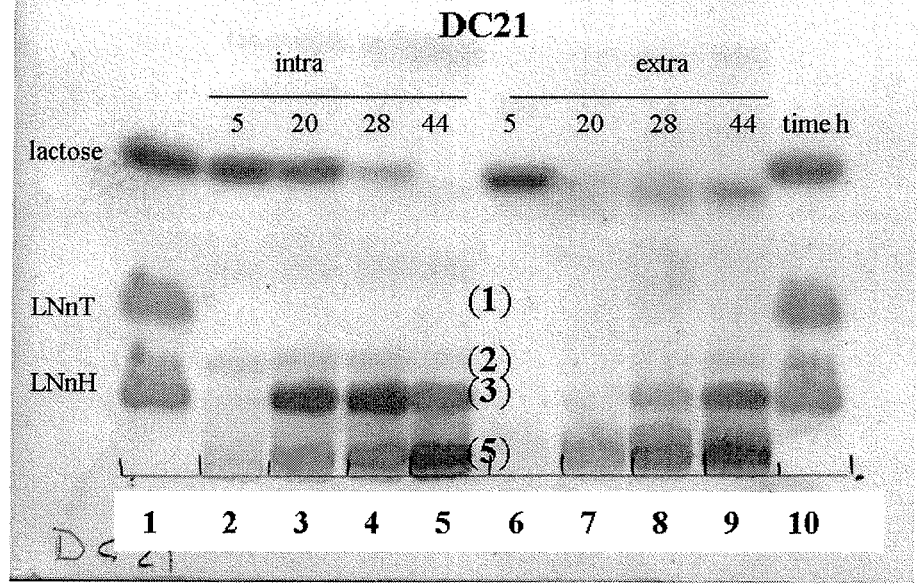
FIG. 14 is a TLC analysis of oligosaccharides produced by high cell density culture of strain DC21 (pBS-cgtAII-nst, pBBR3-SS-gne, pSU-cgtB). The initial lactose concentration was 5 g.l$^{-1}$. Lanes 1 an 10: standard solution (2 mg.ml$^{-1}$ each) of lactose lacto-N-neotetraose (LNnT), lacto-N-neohexaose (LNnH). Lanes 2, 3, 4, 5: intracellular fractions withdrawn 5, 20, 28 and 44 hours after lactose addition. Lanes 6, 7, 8, 9: extracellular fractions withdrawn 5, 20, 28 and 44 hours after lactose addition. Sialyllactose (1) and the GM1 sugar (3) migrate as LNnT and LNnH respectively.

As shown in FIG. 14, the additional expression of gne has almost entirely abolished the accumulation of the isoGM2 sugar and the two major products were the GM1 sugar (3) and the GA1 sugar (5). The GM1 accumulated transiently; its intracellular concentration reached a maximum 28 hours after the lactose addition and then decreased due to the formation of compound (5).

EXAMPLE 9

Production of GM1 Sugar Using the *C. jejuni* Sialyltransferase CstIII

The cstIII gene was cloned by PCR using genomic DNA from *C. jejuni* O:2 strain NCTC 11168 as a template. The cstIII gene was then sub-cloned in a pBluescript plasmid upstream cgtAII. The resulting plasmid pBS-cstIII-cgtAII was used to construct the strain DC22 which also expressed cgtB and the neuBCA genes for CMP-Neu5Ac biosynthesis.

Figure 15:
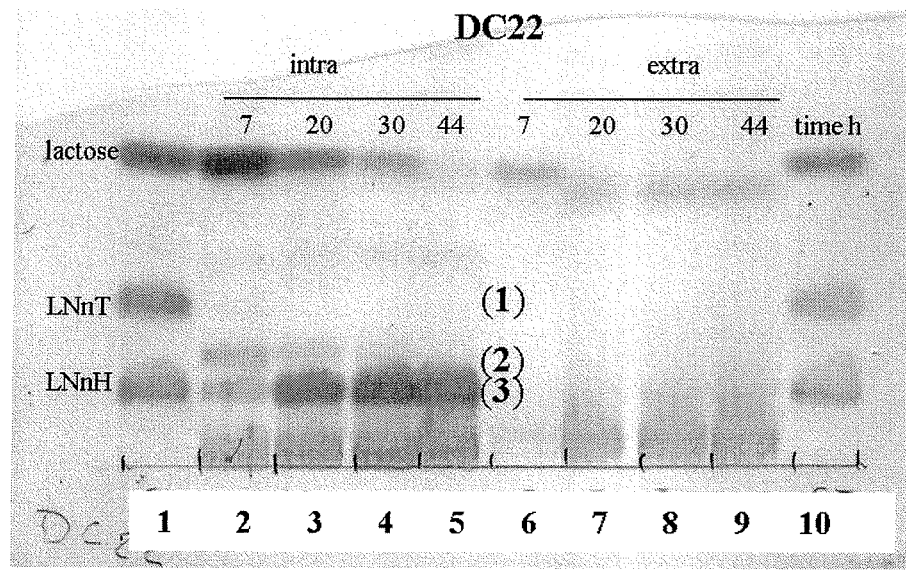
FIG. 15 is a TLC analysis of oligosaccharides produced by high cell density culture of strain DC22. (pBS-cstIII-cgtAII, pBBR3-SS-gne, pSU-cgtB) The initial lactose concentration was 5g.l$^{-1}$. Lanes 1 and 10: standard solution (2 mg.ml$^{-1}$ each) of lactose lacto-N-neotetraose (LNnT), lacto-N-neohexaose (LNnH). Lanes 2, 3, 4, 5: intracellular fractions withdrawn 7, 20, 30 and 44 hours after lactose addition. Lanes 6, 7, 8, 9: extracellular fractions withdrawn 7, 20, 30 and 44 hours after lactose addition. Sialyllactose (1) and the GM1 sugar (3) migrate as LNnT and LNnH respectively.

TLC analysis (FIG. 15) showed that the GM1 sugar (3) was almost the only oligosaccharide found in the intracellular fraction of strain DC22 at the end of the culture. Sialyllactose (1) and the GM2 sugar (2) could be barely detected as intermediate. After purification on Dowex1 as described in example 5, the yield of GM1 sugar was 6 g from a one liter of culture.

EXAMPLE 10

Production of GM2 Sugar

Figure 16:
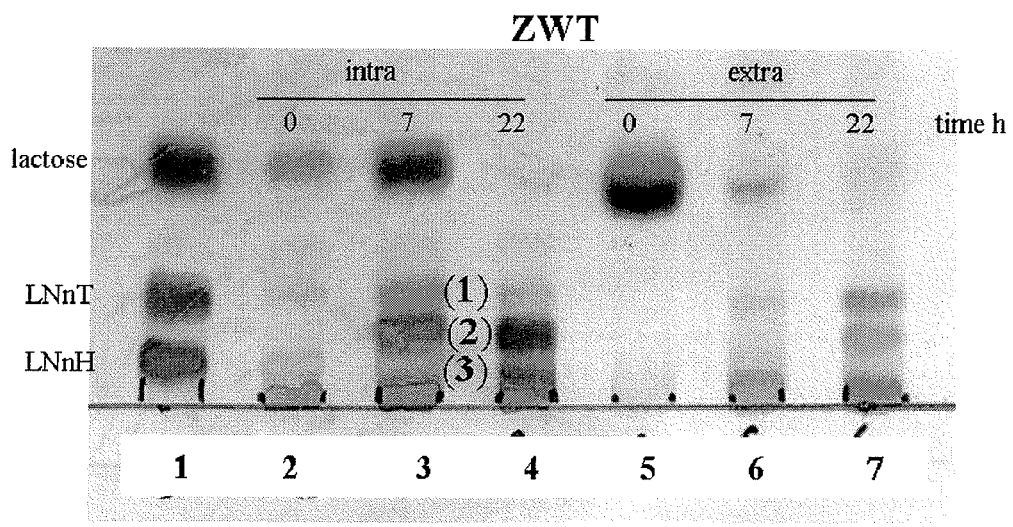
FIG. 16 is a TLC analysis of oligosaccharides produced by high cell density culture of strain ZWT (ZLKA, pBS-nst, pBBR3-SS-gne, pWKS-cgtAII). The initial lactose concentration was 5 g.l$^{-1}$. Lanes 1: standard solution (2 mg.ml$^{-1}$ each) of lactose, lacto-N-neotetraose (LNnT) lacto-N-neohexaose (LNnH). Lanes 2, 3, 4: intracellular fractions withdrawn 0, 7 and 22 hours after lactose addition. Lanes 5, 6, 7: extracellular fractions withdrawn 0, 7, and 22 hours after lactose addition.

The production of the GM2 sugar was investigated with the ZWT strain that was similar to the GM1 producing strain DC21 except it did not expressed the cgtB gene. As shown in FIG. 16, lactose was very rapidly converted by strain ZWT in compounds (2) that migrated as GM2. Surprisingly a compound (3) that migrated slower that GM2 were also produced.

The compounds (2) and (3) were purified from the intracellular fraction of strain ZWT culture by chromatography on Dowex 1. Mass spectrometry analysis indicated that purified compound (2) consisted of a mixture of GM2 sugar and of the GA2 sugar analog.

The ESI⁻ mass spectrum of fraction B showed two peaks at m/z 1310 and 1269.

The peak at m/z 1310 probably corresponds to the quasi-molecular ions $[(M+Na-H)-H f]^-$ derived from the hexasaccharide GalNAcβ-4(Neu5Acα-3)Galβ-4(Neu5Acα-3)Galβ-4Glc which was further designated as GA3 sugar (Table 3). The second peak at m/z 1269 corresponds to the quasi-molecular ions $[(M+Na-H)-H]^-$ derived from the Galβ-4(Neu5Acα-3)Galβ-4(Neu5Acα-3)Galβ-4Glc structure (called GA4 sugar).

The formation of GA3 and GA4 sugar is explained as illustrated in FIG. 11 by a side activity of the Nst sialyltransferase which appears to be able to sialylated the terminal non reducing Gal of the GA2 sugar. The resulting disialylated pentasaccharide (GA6 sugar) can serve as acceptor for the CgtAII to be converted into either GA3 or GA4 sugars

EXAMPLE 11

Construction of galU Mutants

To construct the galU mutant, a 1.88 kb DNA fragment containing the galU sequence was amplified by PCR using the *E. coli* K12 genomic DNA as template and the two following primers: 5'CAATGCCAAATATGGGGAAC (SEQ ID No 16) and 5'GCGGCCGCGTCTTTTCTGGCTAA (SEQ ID No 17)

The amplified fragment was cloned into the pCR4blunt-TOPO vector (Invitrogen) and a 0.244 kb fragment located between the two NdeI sites present in the galU sequence was excised by NdeI digestion. The truncated galU gene was subcloned into the SalI NotI sites of the pKO3 vector. The galU disruption was carried out in strain ZLKA according to the pKO3 gene replacement protocol (Link et al., 1997), yielding to the ZWU host strain.

EXAMPLE 12

Production of GM2 Sugar by galU Mutants

Figure 17:
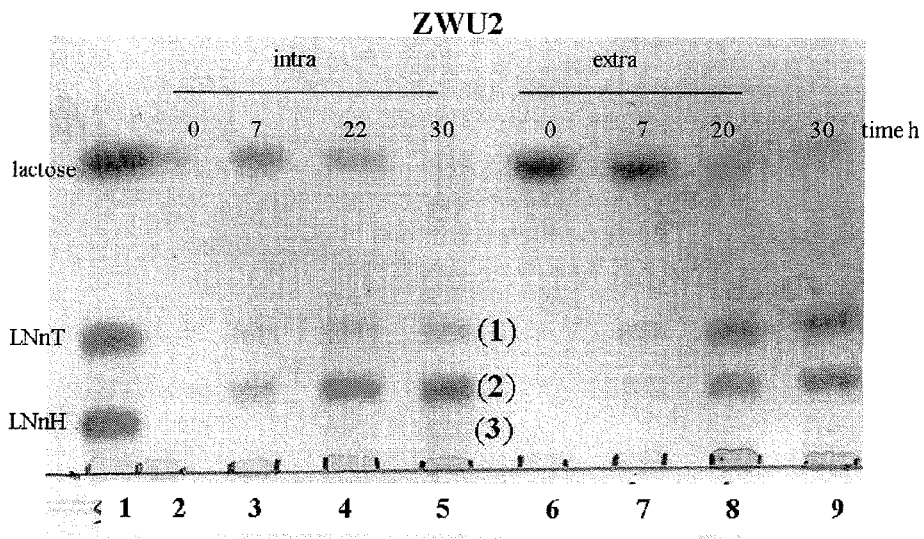
FIG. 17 is a TLC analysis of oligosaccharides produced by high cell density culture of strain ZWU2 (ZWU, pBS-nst, pBBR3-SS-gne, pWKS-cgtAII). The initial lactose concentration was 5 g.l$^{-1}$. Lanes 1: standard solution (2 mg.ml$^{-1}$ each) of lactose, lacto-N-neotaose (LNnT) lacto-N-neohexaose (LNnH). Lanes 2, 3, 4, and 5: intracellular fractions withdrawn 0, 7, 22 and 30 hours after lactose addition. Lanes 6, 7, 8 and 9: extracellular fractions withdrawn 0, 7, 22 and 30 hours after lactose addition.
Figure 18:
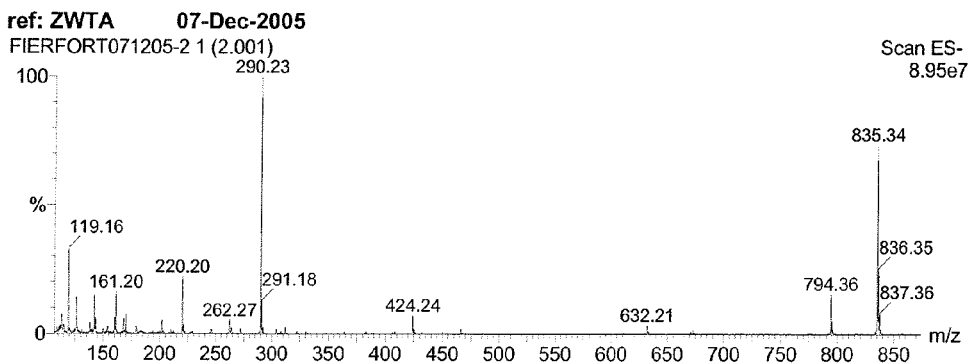
FIG. 18 shows a ESI⁻ mass spectrum of fraction compound (2) purified from the intracellular fraction of control strain ZWT (A) and galU mutant strain ZWU2 (B) Peak at m/z 835 corresponds to GM2 sugar and peak at m/z 794 corresponds to the galactosylated analog (GA2 sugar).
Figure 18:
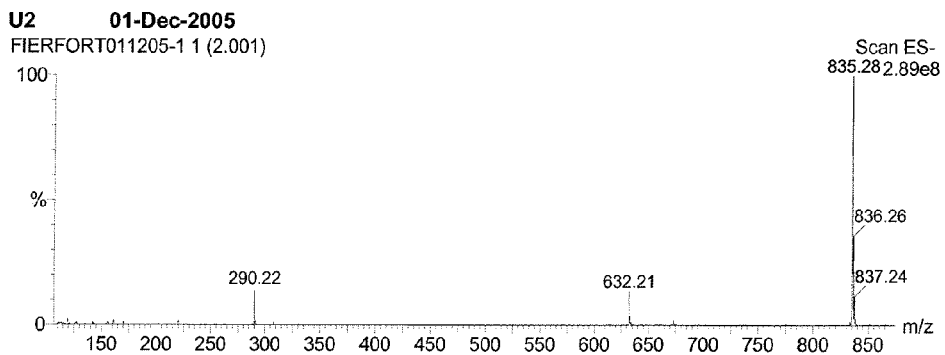

The strain ZWU2 was similar to the ZWT strain used for GM2 sugar production in example 10, except that the galU strain ZWU was used as host strain instead of the ZLKA strain (Table 1) As show in FIG. 17, no more side-products (3) was detected at the end of the ZWU2 culture. In addition mass spectrometry analysis showed that compound (2) was only composed of GM2 sugar and that the GA2 sugar analog, which was present in the compound (2) purified from the ZWT culture, could be detected (FIG. 18).

EXAMPLE 13

Production of GD2 Sugar

First attempt to produce the GD2 sugar was made with the strain NF08 which was constructed by transforming the ZLKA host strain with the three plasmids pUC18-cstII, pBBR3-SS-gne, pWKS-cgtAII (Table 1). Characterization of oligosaccharides produced by strain NF08 showed that the major products were the GM2 sugar and its galactosylated analog GA2 sugar. A small amount of GD2 sugar was also formed but it was purified as a mixture with the galactosylated analogs GA5 and GA6 (FIG. 5).

The cgtAII gene was sub-cloned into the pBAD 33 plasmid under the control of the promotor arabinose ($P_{ara}$). By this way the cgtAII expression could be regulated independently from the other genes which were under the control of the $P_{lac}$ promoter. The strain NF09 containing the pBAD33-cgtAII plasmid instead of pWKS-cgtAII was cultivated without arabinose for first 24 hours that followed the lactose addition (3 g.l⁻¹). Then arabinose was added and the strain was cultivated for an additional period of 24 hours. This strategy effectively resulted in diminution in the GM2 sugar production with a concomitant increase in the GD2 sugar yield. However the galactosylated analogs GA5 or GA6 were still produced in significant amount. To prevent the formation of these analogs, which are very difficult to separate from GD2, the production of GD2 was investigated in the galU mutant strain ZWU1.

Figure 19:
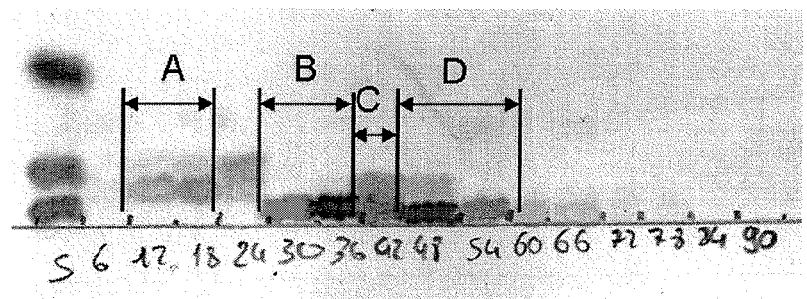
FIG. 19 is a TLC analysis of fractions obtained after separation of the intracellular fraction from a one liter culture of strain ZWU1. The separation was carried out on Dowex 1 (HCO3⁻ form) using a 0-1M NaHCO$_3$ gradient. The volume of each tube was 10 ml. The yield of faction A, B, C and D were 0.5 g, 0.85, 0.6 and 1.2 g respectively.

The strain ZWU1 was similar to the NF09 strain except that the galU strain ZWU was used as host strain instead of the ZLKA strain (Table 1) Arabinose was added after 25 hours of culture to increase the expression of cgtAII after that almost all of the sialyllactose has disappeared. Purification of the intracellular fraction on Dowex1 led to the separation of four fractions (FIG. 19). Mass spectrometry analysis indicated that fraction A was composed of GM2 sugar and that fraction B consisted of GD2 sugar. Fraction C mainly contained GD3 and Fraction D contained GT2 sugars. No galactosylated analogs could be detected and the GD2 sugar was obtained as the major product.

EXAMPLE 14

Production of GD1b and GT1

The two genes cstII and cgtB were cloned in the same pBluescript plasmid (pBS-cstII-cgtB). The strain NF21 was constructed by transforming the ZLKA host strain with plasmid pBS-cstII-cgtB and the two plasmids pBBR-SS-gne and pBAD33-cgtAII. Strain NF21 was cultivated at high cell density as described for strain NF09 in example 13 in conditions that favoured the formation of GD2. Oligosaccharides produced from a one liter culture of strain NF21 were first purified on Dowex 1 (HCO3) resin and three fractions (A, B, and C) were eluted with a NaHCO$_3$ gradient (0-1M).

Mass spectrometry analysis indicated that fraction A (490 mg) contained GD1 sugar, that fraction B (870 mg) contained a mixture of GD1 sugar with GA5 or GA6 analog, and that Fraction C (960 mg) contained GT1 sugar. GD1 and GT1 sugars were purified from Fraction A and C by size exclusion chromatography on a Toyopearl HW40S column using NaHCO3 100 mM as eluant. As shown in Table 4, $^1$H NMR analysis shows that the proton chemical shifts of the H-1 of the terminal galactose of both GD1 and GT1 were very closed to the value of the H-1 of GM1a sugar in which the terminal galactose is unsubstitued. By contrast the signal of the H-1 of the terminal galactose of GD1a and GT1a shifted to 4.62 ppm in reason of its substirution with a sialic acid. These results clearly indicated that the GD1 and GT1 sugars produced by strain NF21 had the structure of GD1b and GT1c.

TABLE 4

NMR proton chemical shift of gangliosides sugars at 343° K

| Strain | Purified sugar | Terminal Galactose | | Internal Galactose | | GalNAc | Glucose | |
|---|---|---|---|---|---|---|---|---|
| | | H-1 | H-3 | H-1 | H-3 | H-1 | αH-1 | βH-1 |
| DC22 | GM1a | 4.57 | 3.84 | 4.56 | 4.17 | 4.83 | 5.25 | 4.68 |
| NF17 | GD1a | 4.62 | 4.11 | 4.54 | 4.17 | 4.83 | 5.25 | 4.68 |
| NF17 | GT1a | 4.62 | nd | 4.53 | nd | 4.83 | 5.25 | 4.68 |
| NF21 | GD1b | 4.55 | nd | 4.53 | nd | 4.83 | 5.25 | 4.68 |
| NF21 | GT1c | 4.55 | 3.81 | 4.52 | 4.17 | 4.83 | 5.25 | 4.68 |

EXAMPLE 15

Production of GT1a Sugar

Figure 20:
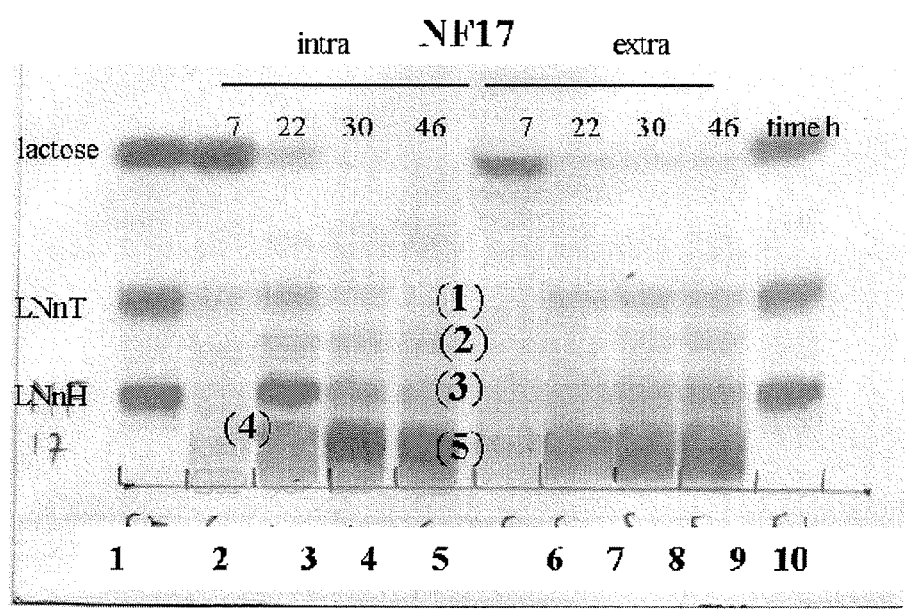
FIG. 20 is a TLC analysis of oligosaccharides produced by high cell density culture of strain NF17 (ZLKA, pBS-cgtA-cstII, pSU-cgtB, pBBR-SS-gne). The initial lactose concentration was 5 g.l⁻¹. Lanes 1 and 10: standard solution (2 mg.ml⁻¹ each) of lactose, lacto-N-neotetraose (LNnT) lacto-N-neohexaose (LNnH). Lanes 2, 3, 4, and 5: intracellular fractions withdrawn 7, 22, 30 and 46 hours after lactose addition. Lanes 6, 7, 8, and 9: extracellular fractions withdrawn 7, 22, 30 and 46 hours after lactose addition.

The two genes cstII and cgtA were cloned in the same pBluescript plasmid to be coexpressed with cgtB and the neuABC genes in a nanKEAT mutant ZLKA host strain (Table 1). The cstII gene was cloned downstream cgtA to have a maximal expression of cgtA and lower expression of cstII in order to minimize the formation of GD3. As shown in FIG. 20, TLC analysis of NF17 culture indicated that compounds migrating like sialyllactose (1) and GM1 sugar (3) were transiently produced. A small amount of compound (2) that migrated as GD3 was recovered at the end of the culture but the main final products were compounds (4) and (5) that migrated slower than GM1. Mass spectrometry analysis of purified compounds indicated that compounds (4) and (5) have a molecular weight corresponding to GD1a and GT1a respectively.

EXAMPLE 16

Production of Sialylgalactose

The GLKA strain was constructed by deleting the nanKEAT genes in the chromosome of the GalK mutant strain GLK (Dumon et al., 2005). The GLK7 strain was obtained by transforming the GLKA strain with the plasmid pBS-nst and pBBR3-SS (Table 1). Cultivation of strain GLK7 at high cell density in presence of 3 g.l$^{-1}$ of galactose resulted in the formation of a disaccharide which was identified to sialylgalactose by mass spectrometry analysis. The sialylgalactose production yield was estimated to be 6 g.l-1 by colorimetric quantification of total sialic acid.

EXAMPLE 17

Production of the Tetrasaccharide Neu5Acα-3Galβ-4GlcNAcβ-4GlcNAc

The plasmid pBS-nst-nodC was constructed by cloning *A. caulinodans* nodC gene from the pBS-nodC plasmid (Cottaz & Samain, 2005) in the EcoRV KpnI sites of pBS-nst. The strain SN4 was obtained by transforming the strain ZLKA with the three plasmids pBS-nst-nodC, pBBR3-SS, pWKS-lgtB-chiA (Table 1). Cultivation of strain SN4 at high cell density resulted in the production of a major oligosaccharide which was identified as Neu5Acα-3Galβ-4GlcNAcβ-4GlcNAc by mass spectrometry analysis.

REFERENCES

Antoine, T., Priem, B., Heyraud, A., Greffe, L., Gilbert, M., Wakarchuk, W. W., Lam, J. S. & Samain, E. (2003). Large-scale in vivo synthesis of the carbohydrate moieties of gangliosides GM1 and GM2 by metabolically engineered *Escherichia coli*. *Chembiochem* 4, 406-412.

Antoine, T., Heyraud, A., Bosso, C. & Samain, E. (2005). Highly efficient biosynthesis of the oligosaccharide moiety of the GD3 ganglioside by using metabolically engineered *Escherichia coli*. *Angew Chem Int Ed Engl* 44, 1350-1352.

Bernatchez, S., Szymanski, C. M., Ishiyama, N., Li, J., Jarrell, H. C., Lau, P. C., Berghuis, A. M., Young, N. M. & Wakarchuk, W. W. (2005). A single bifunctional UDP-GlcNAc/Glc 4-epimerase supports the synthesis of three cell surface glycoconjugates in *Campylobacter jejuni*. *J Biol Chem* 280, 4792-4802.

Bettler, E., Samain, E., Chazalet, V., Bosso, C., Heyraud, A., Joziasse, D. H., Wakarchuk, W. W., Imberty, A. & Geremia, A. R. (1999). The living factory: in vivo production of N-acetyllactosamine containing carbohydrates in *E. coli*. *Glycoconj J* 16, 205-212.

Cottaz, S. & Samain, E. (2005). Genetic engineering of *Escherichia coli* for the production of N(I),N(II)-diacetyl-chitobiose (chitinbiose) and its utilization as a primer for the synthesis of complex carbohydrates. *Metab Eng* 7, 311-317.

Creuzenet, C., Belanger, M., Wakarchuk, W. W. & Lam, J. S. (2000). Expression, purification, and biochemical characterization of WbpP, a new UDP-GlcNAc C4 epimerase from *Pseudomonas aeruginosa* serotype O6. *J Biol Chem* 275, 19060-19067.

Datsenko, K. A. & Wanner, B. L. (2000). One-step inactivation of chromosomal genes in *Escherichia coli* K-12 using PCR products. *Proc Natl Acad Sci USA* 97, 6640-6645.

Dumon, C., Samain, E. & Priem, B. (2004). Assessment of the two *Helicobacter pylori* alpha-1,3-fucosyltransferase ortholog genes for the large-scale synthesis of Lewis×human milk oligosaccharides by metabolically engineered *Escherichia coli*. *Biotechnol Prog* 20, 412-419.

Dumon, C., Bosso, C., Utile, J. P., Heyraud, A. & Samain, E. (2005). Production of Lewis×Tetrasaccharides by Metabolically Engineered *Escherichia coli*. *Chembiochem* 7, 359-365.

Dykxhoorn, D. M., St Pierre, R. & Linn, T. (1996). A set of compatible tac promoter expression vectors. *Gene* 177, 133-136.

Fort, S., Birikaki, L., Dubois, M. P., Antoine, T., Samain, E. & Driguez, H. (2005). Biosynthesis of conjugatable saccharidic moieties of GM2 and GM3 gangliosides by engineered *E. coli. Chem Commun (Camb)*, 2558-2560.

Ganguli, S., Zapata, G., Wallis, T., Reid, C., Boulnois, G., Vann, W. F. & Roberts, I. S. (1994). Molecular cloning and analysis of genes for sialic acid synthesis in *Neisseria meningitidis* group B and purification of the meningococcal CMP-NeuNAc synthetase enzyme. *J Bacteriol* 176, 4583-4589.

Gilbert, M., Bayer, R., Cunningham, A. M., DeFrees, S., Gao, Y., Watson, D. C., Young, N. M. & Wakarchuk, W. W. (1998). The synthesis of sialylated oligosaccharides using a CMP-NeuSAc synthetase/sialyltransferase fusion. *Nat Biotechnol* 16, 769-772.

Gilbert, M., Karwaski, M. F., Bernatchez, S., Young, N. M., Taboada, E., Michniewicz, J., Cunningham, A. M. & Wakarchuk, W. W. (2002). The genetic bases for the variation in the lipo-oligosaccharide of the mucosal pathogen, *Campylobacter jejuni*. Biosynthesis of sialylated ganglioside mimics in the core oligosaccharide. *J Biol Chem* 277, 327-337.

Hamilton, C. M., Aldea, M., Washburn, B. K., Babitzke, P. & Kushner, S. R. (1989). New method for generating deletions and gene replacements in *Escherichia coli. J Bacteriol* 171, 4617-4622.

Kalivoda, K. A., Steenbergen, S. M., Vimr, E. R. & Plumbridge, J. (2003). Regulation of sialic acid catabolism by the DNA binding protein NanR in *Escherichia coli. J Bacteriol* 185, 4806-4815.

Kovach, M. E., Elzer, P. H., Hill, D. S., Robertson, G. T., Farris, M. A., Roop, R. M., 2nd & Peterson, K. M. (1995). Four new derivatives of the broad-host-range cloning vector pBBR1MCS, carrying different antibiotic-resistance cassettes. *Gene* 166, 175-176.

Lee, J., Yi, J., Lee, S., Takahashi, S. & Kim, B. (2004). Production of N-acetylneuraminic acid from N acetylglucosamineand pyruvate using recombinant human renin binding protein and sialic aldolase in one pot. *Enzyme Microb Technol* 35, 121-125.

Link, A. J., Phillips, D. & Church, G. M. (1997). Methods for generating precise deletions and insertions in the genome of wild-type *Escherichia coli:* application to open reading frame characterization. *J Bacteriol* 179, 6228-6237.

Linton, D., Gilbert, M., Hitchen, P. G., Dell, A., Morris, H. R., Wakarchuk, W. W., Gregson, N. A. & Wren, B. W. (2000). Phase variation of a beta-1,3 galactosyltransferase involved in generation of the ganglioside GM1-like lipo-oligosaccharide of *Campylobacter jejuni. Mol Microbiol* 37, 501-514.

Martinez, E., Bartolome, B. & de la Cruz, F. (1988). pACYC184-derived cloning vectors containing the multiple cloning site and lacZ alpha reporter gene of pUC8/9 and pUC18/19 plasmids. *Gene* 68, 159-162.

Maru, I., Ohnishi, J., Ohta, Y. & Tsukada, Y. (1998). Simple and large-scale production of N-acetylneuraminic acid from N-acetyl-D-glucosamine and pyruvate using N-acyl-D-glucosamine 2-epimerase and N-acetylneuraminate lyase. *Carbohydr Res* 306, 575-578.

Plumbridge, J. & Vimr, E. (1999). Convergent pathways for utilization of the amino sugars N-acetylglucosamine, N-acetylmannosamine, and N-acetylneuraminic acid by *Escherichia coli. J Bacteriol* 181, 47-54.

Priem, B., Gilbert, M., Wakarchuk, W. W., Heyraud, A. & Samain, E. (2002). A new fermentation process allows large-scale production of human milk oligosaccharides by metabolically engineered bacteria. *Glycobiology* 12, 235-240.

Samain, E., Drouillard, S., Heyraud, A., Driguez, H. & Geremia, R. A. (1997). Gram-scale synthesis of recombinant chitooligosaccharides in *Escherichia coli. Carbohydr Res* 302, 35-42.

Stapleton, A. E., Stroud, M. R., Hakomori, S. I. & Stamm, W. E. (1998). The globoseries glycosphingolipid sialosyl galactosyl globoside is found in urinary tract tissues and is a preferred binding receptor In vitro for uropathogenic *Escherichia coli* expressing pap-encoded adhesins. *Infect Immun* 66, 3856-3861.

Vann, W. F., Tavarez, J. J., Crowley, J., Vimr, E. & Silver, R. P. (1997). Purification and characterization of the *Escherichia coli* K1 neuB gene product N-acetylneuraminic acid synthetase. *Glycobiology* 7, 697-701.

Vann, W. F., Daines, D. A., Murkin, A. S., Tanner, M. E., Chaffm, D. O., Rubens, C. E., Vionnet, J. & Silver, R. P. (2004). The NeuC protein of *Escherichia coli* K1 is a UDP N-acetylglucosamine 2-epimerase. *J Bacteriol* 186, 706-712.

Varki, A. (1993). Biological roles of oligosaccharides: all of the theories are correct. *Glycobiology* 3, 97-130.

Vimr, E. R. & Troy, F. A. (1985). Identification of an inducible catabolic system for sialic acids (nan) in *Escherichia coli. J Bacteriol* 164, 845-853.

Wang, R. F. & Kushner, S. R. (1991). Construction of versatile low-copy-number vectors for cloning, sequencing and gene expression in *Escherichia coli. Gene* 100, 195-199.

Werner, I. & Odin, L. (1952). On the presence of sialic acid in certain glycoproteins and in gangliosides. *Acta Soc Med Ups* 57, 230-241.

Yamamoto, T., Nakashizuka, M. & Terada, I. (1998). Cloning and expression of a marine bacterial beta-galactoside alpha2,6-sialyltransferase gene from *Photobacterium damsela* JT0160. *J Biochem (Tokyo)* 123, 94-100.

Zhang, X. & Kiechle, F. L. (2004). Review: Glycosphingolipids in health and disease. *Ann Clin Lab Sci* 34, 3-13.

What is claimed is:

1. A method for producing a sialylated oligosaccharide, comprising:
   a) culturing an *Escherichia coli* microorganism, comprising heterologous genes encoding a CMP-Neu5Ac synthetase, a sialic acid synthase, a GlcNAc-6-phosphate 2 epimerase and a sialyltransferase, wherein endogenous genes coding for sialic acid aldolase (NanA) and for ManNac kinase (NanK) have been deleted or inactivated, and wherein said microorganism produces internally, activated sialic acid as donor substrate for said sialyltransferase; and
   b) culturing said microorganism in a culture medium comprising an exogenous precursor selected from the group consisting of lactose, galactose, β-galactoside, and α-galactoside, wherein active uptake into the microorganism of said exogenous precursor occurs and wherein said exogenous precursor is the acceptor substrate for said sialytransferase for producing the sialylated oligosaccharide.

2. The method according to claim 1, wherein the sialyltransferase is α-2,3-sialyltransferase, α-2,3- and α-2,8-sialyltransferase (cstII), or α-2,6 sialyltransferase.

3. The method according to claim 1, wherein the CMP-Neu5Ac synthetase is neuA, the sialic acid synthase is neuB, and the GlcNAc-6-phosphate 2 epimerase is neuC.

4. The method according to claim 1, further comprising deletion or inactivation of nanT and nanE genes in the microorganism.

5. The method according to claim 1, wherein said microorganism is LacY+ (β-galactoside permease), LacZ– (β galactosidase), and optionally MelA– (α-galactosidase).

6. The method according to claim 1, wherein the α-galactoside is globotriose (Galα-4Galβ-4Glc).

7. A microorganism, wherein said microorganism is an *Escherichia coli* strain, comprising heterologous genes encoding a CMP-Neu5Ac synthetase, a sialic acid synthase, a GlcNAc-6-phosphate 2 epimerase and a sialyltransferase, wherein endogenous genes coding for sialic acid aldolase (NanA) and for ManNac kinase (NanK) have been deleted or inactivated, and wherein said microorganism produces internally, activated sialic acid as donor substrate for said sialytransferase.

8. A cell culture medium comprising lactose and the microorganism of claim 7, wherein the heterologous sialyltransferase gene is α-2,3-sialyltransferase, α-2,3- and α-2,8-sialyltransferase (cstII), or α-2,6 sialyltransferase.

9. The method according to claim 1, wherein the sialylated oligosaccharide is 3'sialyllactose or 6'sialyllactose, comprising culturing said microorganism in a culture medium at high cell density on a carbon substrate selected from the group consisting of glucose and glycerol, and fed with lactose which is internalized by the lactose permease of said microorganism and sialylated by said recombinant sialyltransferase of said microorganism using CMP-Neu5Ac endogenously generated from UDP-GlcNAc.

10. The method according to claim 9,
   wherein the microorganism further comprises heterologous sequences encoding β-1,4GalNActransferase and β-1,3-Galactosyltransferase, and
   wherein the method further comprises
   β-1,4GalNActransferase transferring a UDP-GalNac residue to sialyllactose (GM3) to form GalNAcβ-4 (Neu5Acα-3)Galβ-4Glc (GM2) and
   β-1,3-Galactosyltransferase transferring a Galactosyl residue to GM2 to form a carbohydrate portion of ganglioside Galβ-3GalNAcβ-4(Neu5Acα-3)Galβ4Glc (GM1).

11. The method according to claim 9, wherein the sialyltransferase is α-2,3- and α-2,8-sialyltransferase (cstII), and wherein the method produces Neu5Acα-3Galβ-3GalNAcβ-4(Neu5Acα-3)Galβ-4Glc (GD1a) and Galβ-3GalNAcβ-4(Neu5Acα-3)Galβ-3GalNAcβ-4(Neu5Acα-3)Galβ-4Glc (GA1).

12. The method according to claim 1, wherein the sialyl transferase is a α-2,3-Sialyltransferase, and wherein the microorganism further comprises a heterologous lgtA gene encoding β-1,3-GlcNAc transferase and a heterologous lgtB gene encoding β-1,4-Galactosyltransferase.

13. The method according to claim 1, for producing sialyl-galactose (Neu5Acα-3Gal) and sialylated oligosaccharides with a terminal reducing galactose, wherein the microorganism is galK−, nanA− and nanK− and expresses the gene for sialyltransferase and the neuBCA genes and is cultured in a medium with galactose.

14. The method according to claim 9, wherein the microorganism is growing on glycerol as carbon substrate.

15. A microorganism, wherein said microorganism is an *Escherichia coli* strain, comprising heterologous genes encoding a CMP-Neu5Ac synthetase, a sialic acid synthase, a GlcNAc-6-phosphate 2 epimerase and a sialyltransferase, wherein endogenous genes coding for sialic acid aldolase (NanA) and for ManNac kinase (NanK) have been deleted or inactivated, wherein said microorganism produces internally, activated sialic acid as donor substrate for said sialyltransferase, and wherein said *Escherichia coli* strain is LacY+ (β-galactoside permease), LacZ− (β-galactosidase), and optionally MelA− (α-galactosidase).

16. The microorganism of claim 15, wherein the sialyltransferase is α-2,3-sialyltransferase, α-2,3- and α-2,8-sialyltransferase (cstII), or α-2,6 sialyltransferase.

* * * * *

SEQUENCE LISTING

```
<160> NUMBER OF SEQ ID NOS: 19

<210> SEQ ID NO 1
<211> LENGTH: 876
<212> TYPE: DNA
<213> ORGANISM: Campylobacter jejuni
<220> FEATURE:
<223> OTHER INFORMATION: Campylobacter glycosyltransferases
<300> PUBLICATION INFORMATION:
```

<308> DATABASE ACCESSION NUMBER: NCBI AR271701
<309> DATABASE ENTRY DATE: 2003-04-10
<313> RELEVANT RESIDUES IN SEQ ID NO: (1)..(876)

<400> SEQUENCE: 1

```
atgaaaaaag ttattattgc tggaaatgga ccaagtttaa aagaaattga ttattcaagg    60
ctaccaaatg attttgatgt atttagatgc aatcaatttt attttgaaga taaatactat   120
cttggtaaaa aattcaaagc agtattttac aatcctggtc ttttttttga acaatactac   180
actttaaaac atttaatcca aaatcaagaa tatgagaccg aactaattat gtgttctaat   240
tacaaccaag ctcatctaga aaatgaaaat tttgtaaaaa cttttacga ttattttcct    300
gatgctcatt tgggatatga tttttttaaa caacttaaag aatttaatgc ttattttaaa   360
tttcacgaaa tttatctcaa tcaaagaatt acctcaggag tctatatgtg tgcagtagct   420
atagccctag atacaaaga aatttatctt tctggaattg attttatca aatgggtca     480
tcttatgctt ttgataccaa acaagaaaat cttttaaaac tggctcctga ttttaaaaat   540
gatcgctcac actatatcgg acatagtaaa aatacagata taaaagcttt agaatttcta   600
gaaaaaactt acaaaataaa actatattgc ttatgtccta acagtctttt agcaaatttt   660
atagaactag cgccaaattt aaattcaaat tttatcatac aagaaaaaaa taactacact   720
aaagatatac tcataccttc tagtgaggct tatggaaaat tttcaaaaaa tattaatttt   780
aaaaaaataa aaattaaaga aaatatttat tacaagttga aaaagatct attaagatta   840
cctagtgata taaagcatta tttcaaagga aaataa                             876
```

<210> SEQ ID NO 2
<211> LENGTH: 876
<212> TYPE: DNA
<213> ORGANISM: Campylobacter jejuni
<220> FEATURE:
<223> OTHER INFORMATION: Alpha-2,3/alpha 2,8-sialyltransferase Campylobacter sialyltransferase II
<300> PUBLICATION INFORMATION:
<308> DATABASE ACCESSION NUMBER: NCBI AX934427
<309> DATABASE ENTRY DATE: 2004-01-05
<313> RELEVANT RESIDUES IN SEQ ID NO: (1)..(876)

<400> SEQUENCE: 2

```
atgaaaaaag ttattattgc tggaaatgga ccaagtttaa aagaaattga ttattcaagg    60
ctaccaaatg attttgatgt atttagatgc aatcaatttt attttgaaga taaatactat   120
cttggtaaaa aattcaaagc agtattttac aatcctggtc ttttttttga acaatactac   180
actttaaaac atttaatcca aaatcaagaa tatgagaccg aactaattat gtgttctaat   240
tacaaccaag ctcatctaga aaatgaaaat tttgtaaaaa cttttacga ttattttcct    300
gatgctcatt tgggatatga tttttttaaa caacttaaag aatttaatgc ttattttaaa   360
tttcacgaaa tttatctcaa tcaaagaatt acctcaggag tctatatgtg tgcagtagct   420
atagccctag atacaaaga aatttatctt tctggaattg attttatca aatgggtca     480
tcttatgctt ttgataccaa acaagaaaat cttttaaaac tggctcctga ttttaaaaat   540
gatcgctcac actatatcgg acatagtaaa aatacagata taaaagcttt agaatttcta   600
gaaaaaactt acaaaataaa actatattgc ttatgtccta acagtctttt agcaaatttt   660
atagaactag cgccaaattt aaattcaaat tttatcatac aagaaaaaaa taactacact   720
aaagatatac tcataccttc tagtgaggct tatggaaaat tttcaaaaaa tattaatttt   780
aaaaaaataa aaattaaaga aaatatttat tacaagttga aaaagatct attaagatta   840
cctagtgata taaagcatta tttcaaagga aaataa                             876
```

<210> SEQ ID NO 3
<211> LENGTH: 876
<212> TYPE: DNA
<213> ORGANISM: Campylobacter jejuni
<220> FEATURE:
<223> OTHER INFORMATION: Campylobacter glycosyltransferases
<300> PUBLICATION INFORMATION:
<308> DATABASE ACCESSION NUMBER: NCBI AR271702
<309> DATABASE ENTRY DATE: 2003-04-10
<313> RELEVANT RESIDUES IN SEQ ID NO: (1)..(876)

<400> SEQUENCE: 3

| | | |
|---|---|---|
| atgaaaaaag ttattattgc tggaaatgga ccaagtttaa aagaaattga ttattcaaga | 60 |
| ctaccaaatg attttgatgt atttagatgc aatcaatttt attttgaaga taaatactat | 120 |
| cttggtaaaa aatgcaaagc agtatttac atcctagtc ttttttttga acaatactac | 180 |
| actttaaaac atttaatcca aaatcaagaa tatgagaccg aactaatcat gtgttctaat | 240 |
| tttaaccaag ctcatctaga aaatcaaaat tttgtaaaaa cttttacga ttattttcct | 300 |
| gatgctcatt tgggatatga ttttttcaaa caacttaaag aattcaatgc ttattttaaa | 360 |
| tttcacgaaa tttatttcaa tcaagaatt acctcagggg tctatatgtg cacagtagcc | 420 |
| atagccctag gatacaaaga aatttatctt tcgggaattg attttatca aaatggatca | 480 |
| tcttatgctt ttgataccaa acaaaaaaat cttttaaaat tggctcctaa ttttaaaaat | 540 |
| gataattcac actatatcgg acatagtaaa aatacagata taaaagcttt agaatttcta | 600 |
| gaaaaaactt acgaaataaa gctatattgt ttatgtccta acagtctttt agcaaatttt | 660 |
| atagaactag cgccaaattt aaattcaaat tttatcatac aagaaaaaaa taactatact | 720 |
| aaagatatac tcataccttc tagtgaggct tatggaaaat ttacaaaaaa tattaatttt | 780 |
| aaaaaaataa aaattaaaga aatatttat tacaagttga taaagatct attaagatta | 840 |
| cctagtgata taaagcatta tttcaaagga aaataa | 876 |

<210> SEQ ID NO 4
<211> LENGTH: 876
<212> TYPE: DNA
<213> ORGANISM: Campylobacter jejuni
<220> FEATURE:
<223> OTHER INFORMATION: Campylobacter glycosyltransferases
<300> PUBLICATION INFORMATION:
<308> DATABASE ACCESSION NUMBER: NCBI AX934429
<309> DATABASE ENTRY DATE: 2004-01-05
<313> RELEVANT RESIDUES IN SEQ ID NO: (1)..(876)

<400> SEQUENCE: 4

| | | |
|---|---|---|
| atgaaaaaag ttattattgc tggaaatgga ccaagtttaa aagaaattga ttattcaaga | 60 |
| ctaccaaatg attttgatgt atttagatgc aatcaatttt attttgaaga taaatactat | 120 |
| cttggtaaaa aatgcaaagc agtatttac atcctagtc ttttttttga acaatactac | 180 |
| actttaaaac atttaatcca aaatcaagaa tatgagaccg aactaatcat gtgttctaat | 240 |
| tttaaccaag ctcatctaga aaatcaaaat tttgtaaaaa cttttacga ttattttcct | 300 |
| gatgctcatt tgggatatga ttttttcaaa caacttaaag aattcaatgc ttattttaaa | 360 |
| tttcacgaaa tttatttcaa tcaagaatt acctcagggg tctatatgtg cacagtagcc | 420 |
| atagccctag gatacaaaga aatttatctt tcgggaattg attttatca aaatggatca | 480 |
| tcttatgctt ttgataccaa acaaaaaaat cttttaaaat tggctcctaa ttttaaaaat | 540 |
| gataattcac actatatcgg acatagtaaa aatacagata taaaagcttt agaatttcta | 600 |
| gaaaaaactt acgaaataaa gctatattgt ttatgtccta acagtctttt agcaaatttt | 660 |

```
atagaactag cgccaaattt aaattcaaat tttatcatac aagaaaaaaa taactatact    720
aaagatatac tcataccttc tagtgaggct tatggaaaat ttacaaaaaa tattaattt     780 aaaaaaataa aaattaaaga aaatatttat tacaagttga taaaagatct attaagatta   840
cctagtgata taaagcatta tttcaaagga aaataa                             876
```

```
<210> SEQ ID NO 5
<211> LENGTH: 1116
<212> TYPE: DNA
<213> ORGANISM: Neisseria meningitidis
<220> FEATURE:
<223> OTHER INFORMATION: nst alpha-2,3-sialyltransferase
<300> PUBLICATION INFORMATION:
<308> DATABASE ACCESSION NUMBER: GENBANK U60660
<309> DATABASE ENTRY DATE: 1996-11-08
<313> RELEVANT RESIDUES IN SEQ ID NO: (573)..(1688)

<400> SEQUENCE: 5
```

```
atgggcttga aaaggcttg tttgaccgtg ttgtgtttga ttgttttttg tttcgggata     60 tttatacat ttgaccgggt aaatcagggg gaaaggaatg cggtttccct gctgaaggag    120
aaacttttca atgaagaggg ggaaccggtc aatctgattt tctgttatac catattgcag   180
atgaaggtgg cggaaaggat tatggcgcag catccgggcg agcggtttta tgtggtgctg   240
atgtctgaaa acaggaatga aaaatacgat tattatttca atcagataaa ggataaggcg   300
gagcgggcgt actttttcca cctgccctac ggtttgaaca atcgtttaa tttcattccg    360 acgatggcgg agctgaaggt aaagtcgatg ctgctgccga agtcaagcg gatttatttg    420 gcaagtttgg aaaaagtcag cattgccgcc ttttttgagca cttacccgga tgcggaaatc    480
aaaacctttg acgacgggac aggcaattta attcaaagca gcagctattt gggcgatgag   540
ttttctgtaa acgggacgat caagcggaat tttgcccgga tgatgatcgg agattggagc   600
atcgccaaaa cccgcaatgc ttccgacgag cattacacga tattcaaggg tttgaaaaac   660
attatggacg acggccgccg caagatgact tacctgccgc tgttcgatgc gtccgaactg   720
aagacggggg acgaaacggg cggcacggtg cggatacttt tgggttcgcc cgacaaagag   780
atgaaggaaa tttcggaaaa ggcggcaaaa aacttcaaaa tacaatatgt cgcgccgcat   840
ccccgccaaa cctacgggct ttccggcgta accacattaa attcgcccta tgtcatcgaa   900
gactatattt tgcgcgagat taagaaaaac ccgcatacga ggtatgaaat ttataccttt   960
ttcagcggcg cggcgttgac gatgaaggat tttcccaatg tgcacgttta cgcattgaaa  1020
ccggcttccc ttccggaaga ttattggctc aagccggtgt atgccctgtt tacccaatcc  1080
ggcatcccga tttttgacatt tgacgataaa aattaa                           1116
```

```
<210> SEQ ID NO 6
<211> LENGTH: 371
<212> TYPE: PRT
<213> ORGANISM: Neisseria meningitidis
<220> FEATURE:
<223> OTHER INFORMATION: Alpha-2,3-sialyltransferase
<300> PUBLICATION INFORMATION:
<308> DATABASE ACCESSION NUMBER: GENBANK AAC44541.1
<309> DATABASE ENTRY DATE: 1996-11-07
<313> RELEVANT RESIDUES IN SEQ ID NO: (1)..(371)

<400> SEQUENCE: 6
```

```
Met Gly Leu Lys Lys Ala Cys Leu Thr Val Leu Cys Leu Ile Val Phe
1               5                   10                  15

Cys Phe Gly Ile Phe Tyr Thr Phe Asp Arg Val Asn Gln Gly Glu Arg
            20                  25                  30
```

Asn Ala Val Ser Leu Leu Lys Glu Lys Leu Phe Asn Glu Glu Gly Glu
            35                  40                  45

Pro Val Asn Leu Ile Phe Cys Tyr Thr Ile Leu Gln Met Lys Val Ala
 50                  55                  60

Glu Arg Ile Met Ala Gln His Pro Gly Glu Arg Phe Tyr Val Val Leu
 65                  70                  75                  80

Met Ser Glu Asn Arg Asn Glu Lys Tyr Asp Tyr Tyr Phe Asn Gln Ile
                85                  90                  95

Lys Asp Lys Ala Glu Arg Ala Tyr Phe Phe His Leu Pro Tyr Gly Leu
            100                 105                 110

Asn Lys Ser Phe Asn Phe Ile Pro Thr Met Ala Glu Leu Lys Val Lys
            115                 120                 125

Ser Met Leu Leu Pro Lys Val Lys Arg Ile Tyr Leu Ala Ser Leu Glu
    130                 135                 140

Lys Val Ser Ile Ala Ala Phe Leu Ser Thr Tyr Pro Asp Ala Glu Ile
145                 150                 155                 160

Lys Thr Phe Asp Asp Gly Thr Gly Asn Leu Ile Gln Ser Ser Ser Tyr
                165                 170                 175

Leu Gly Asp Glu Phe Ser Val Asn Gly Thr Ile Lys Arg Asn Phe Ala
            180                 185                 190

Arg Met Met Ile Gly Asp Trp Ser Ile Ala Lys Thr Arg Asn Ala Ser
        195                 200                 205

Asp Glu His Tyr Thr Ile Phe Lys Gly Leu Lys Asn Ile Met Asp Asp
    210                 215                 220

Gly Arg Arg Lys Met Thr Tyr Leu Pro Leu Phe Asp Ala Ser Glu Leu
225                 230                 235                 240

Lys Thr Gly Asp Glu Thr Gly Val Thr Val Arg Ile Leu Leu Gly Ser
                245                 250                 255

Pro Asp Lys Glu Met Lys Glu Ile Ser Glu Lys Ala Ala Lys Asn Phe
            260                 265                 270

Lys Ile Gln Tyr Val Ala Pro His Pro Arg Gln Thr Tyr Gly Leu Ser
        275                 280                 285

Gly Val Thr Thr Leu Asn Ser Pro Tyr Val Ile Glu Asp Tyr Ile Leu
    290                 295                 300

Arg Glu Ile Lys Lys Asn Pro His Thr Arg Tyr Glu Ile Tyr Thr Phe
305                 310                 315                 320

Phe Ser Gly Ala Ala Leu Thr Met Lys Asp Phe Pro Asn Val His Val
                325                 330                 335

Tyr Ala Leu Lys Pro Ala Ser Leu Pro Glu Asp Tyr Trp Leu Lys Pro
            340                 345                 350

Val Tyr Ala Leu Phe Thr Gln Ser Gly Ile Pro Ile Leu Thr Phe Asp
        355                 360                 365

Asp Lys Asn
    370

<210> SEQ ID NO 7
<211> LENGTH: 933
<212> TYPE: DNA
<213> ORGANISM: Neisseria meningitidis
<220> FEATURE:
<223> OTHER INFORMATION: LgtC gene
<300> PUBLICATION INFORMATION:
<308> DATABASE ACCESSION NUMBER: GENBANK U65788
<309> DATABASE ENTRY DATE: 1999-12-08
<313> RELEVANT RESIDUES IN SEQ ID NO: (661)..(1596)

<400> SEQUENCE: 7

-continued

```
atggacatcg tatttgcggc agacgacaac tatgccgcct atctttgcgt tgcggcaaaa    60
agcgtggaag cggcccatcc cgatacggaa atcaggttcc acgtcctcga tgccggcatc   120
agtgaggcaa accgggcggc ggttgctgcc aatttgcggg ggggggtaa tatccgcttt    180
atagacgtaa accccgaaga tttcgccggc ttccccttaa acatcaggca catttccatc   240
acgacttatg cccgcttgaa attgggcgaa tacattgccg attgcgataa agtcctgtat   300
ctggatatag acgtattggt cagggacagc ctgaagccct atgggatac cgatttgggc    360
gataactggc ttggcgcgtg catcgatttg tttgtcgaaa ggcagaatgc ttacaaacaa   420
aaaatcggta tggcggacgg agaatattat ttcaatgccg gcgtattgct gatcaacctg   480
aaaaagtggc ggcagcacga tattttcaaa atggcctgcg aatgggtgga acaatacaag   540
gacgtgatgc aatatcagga tcaggatatt ttgaacgggc tgtttaaagg cggggtgtgt   600
tatgcgaaca gccgtttcaa ctttatgccg accaatgatg cctttatggc gaacaggttt   660
gcgtcccgcc ataccgaccc gctttaccgc gaccggactt atacggcgat gcctgtcgcc   720
gtcagccatt attgcggccc ggcaaagccg tggcacaggg actgcaccgc gtggggtgcg   780
gaacgtttca cagaattggc gggcagcctg acgagcgttc ccgaagaatg gcgcggcaaa   840
cttgccgtcc cgcaccgtgt gtttccgaca aagcgtatgc ttcaaagatg gcgcagaaag   900
ctgtctgcca gattcttacg caagatttat tga                                933
```

<210> SEQ ID NO 8
<211> LENGTH: 323
<212> TYPE: PRT
<213> ORGANISM: Neisseria meningitidis
<220> FEATURE:
<223> OTHER INFORMATION: LgTC protein
<300> PUBLICATION INFORMATION:
<308> DATABASE ACCESSION NUMBER: GENBANK AAB48385
<309> DATABASE ENTRY DATE: 1999-12-08
<313> RELEVANT RESIDUES IN SEQ ID NO: (1)..(323)

<400> SEQUENCE: 8

```
Met Glu Asn Cys Pro Leu Val Ser Val Ile Val Cys Ala Tyr Asn Ala
1               5                   10                  15

Glu Gln Tyr Ile Asp Glu Ser Ile Ser Ser Ile Ile Asn Gln Thr Tyr
            20                  25                  30

Glu Asn Leu Glu Ile Ile Val Ile Asn Asp Gly Ser Thr Asp Leu Thr
        35                  40                  45

Leu Ser His Leu Glu Glu Ile Ser Lys Leu Asp Lys Arg Ile Lys Ile
    50                  55                  60

Ile Ser Asn Lys Tyr Asn Leu Gly Phe Ile Asn Ser Leu Asn Ile Gly
65                  70                  75                  80

Leu Gly Cys Phe Ser Gly Lys Tyr Phe Ala Arg Met Asp Ala Asp Asp
                85                  90                  95

Ile Ala Lys Pro Ser Trp Ile Glu Lys Ile Val Thr Tyr Leu Glu Lys
            100                 105                 110

Asn Asp His Ile Thr Ala Met Gly Ser Tyr Leu Glu Ile Ile Val Glu
        115                 120                 125

Lys Glu Cys Gly Ile Ile Gly Ser Gln Tyr Lys Thr Gly Asp Ile Trp
    130                 135                 140

Lys Asn Pro Leu Leu His Asn Asp Ile Cys Glu Ala Met Leu Phe Tyr
145                 150                 155                 160

Asn Pro Ile His Asn Asn Thr Met Ile Met Arg Ala Asn Val Tyr Arg
                165                 170                 175
```

-continued

```
Glu His Lys Leu Ile Phe Asn Lys Asp Tyr Pro Tyr Ala Glu Asp Tyr
            180                 185                 190

Lys Phe Trp Ser Glu Val Ser Arg Leu Gly Cys Leu Ala Asn Tyr Pro
        195                 200                 205

Glu Ala Leu Val Lys Tyr Arg Leu His Gly Asn Gln Thr Ser Ser Val
    210                 215                 220

Tyr Asn His Glu Gln Asn Glu Thr Ala Lys Lys Ile Lys Arg Glu Asn
225                 230                 235                 240

Ile Thr Tyr Tyr Leu Asn Lys Ile Gly Ile Asp Lys Val Ile Asn
                245                 250                 255

Ser Val Ser Leu Leu Glu Ile Tyr His Val Asp Lys Ser Asn Lys Val
                260                 265                 270

Leu Lys Ser Ile Leu Tyr Glu Met Tyr Met Ser Leu Asp Lys Tyr Thr
        275                 280                 285

Ile Thr Ser Leu Leu His Phe Ile Lys Tyr His Leu Glu Leu Phe Asp
        290                 295                 300

Leu Lys Gln Asn Leu Lys Ile Ile Lys Lys Phe Ile Arg Lys Ile Asn
305                 310                 315                 320

Val Ile Phe
```

<210> SEQ ID NO 9
<211> LENGTH: 972
<212> TYPE: DNA
<213> ORGANISM: Haemophilus influenzae
<220> FEATURE:
<223> OTHER INFORMATION: lgtD gene
<300> PUBLICATION INFORMATION:
<308> DATABASE ACCESSION NUMBER: GENBANK U32832
<309> DATABASE ENTRY DATE: 2004-06-02
<313> RELEVANT RESIDUES IN SEQ ID NO: (641)..(1612)

<400> SEQUENCE: 9

```
atggaaaatt gtccattagt atcggttatt gtttgtgctt ataacgctga gcaatatata    60
gatgaaagca tttcatccat tattaatcag acttatgaaa tctagaaat tatagttatc   120
aatgatggtt caacagattt gactttgtct catttagaag aaatatctaa attagataaa   180
aggataaaaa ttatcagtaa taaatataat ttagggttca taaattcttt gaatataggc   240
cttggttgtt tttcaggtaa atattttgca agaatggatg ctgatgatat agctaaacca   300
tcgtggattg agaaaatagt tacctatctg gagaaaaatg atcatattac agcaatggga   360
tcatacttag agattattgt agaaaaagaa tgtggaatta tcggttctca atataaaact   420
ggagatatat ggaaaaatcc attgctacat aatgatattt gtgaagctat gcttttctat   480
aatccgatac ataacaacac tatgattatg agagcaaatg tatatagaga gcataaatta   540
atctttaata aagattatcc gtatgcagaa gattataagt tttggtcaga ggttagtagg   600
cttggttgtt tagctaatta tcctgaagca ttagtaaaat atagactaca tggaaaccaa   660
acatcatcag tttataatca tgagcaaaat gagacagcta aaagataaa gagggaaaat   720
attacatatt accttaataa gataggtata gatataaaag taattaatag tgtgtcgttg   780
ctagaaatat atcatgtgga taaagtaat aaagtgttga aaagtatact ttatgagatg   840
tatatgagct tagataaata tactataact tcactcttac attttattaa atatcatctt   900
gaattatttg atttaaagca aaattaaag attataaaaa agttcataag aaaaataaat   960
gttatatttt ag                                                       972
```

<210> SEQ ID NO 10
<211> LENGTH: 323

```
<212> TYPE: PRT
<213> ORGANISM: Haemophilus influenzae
<220> FEATURE:
<223> OTHER INFORMATION: lgtD
<300> PUBLICATION INFORMATION:
<308> DATABASE ACCESSION NUMBER: GENBANK AAC23227
<309> DATABASE ENTRY DATE: 2005-12-21
<313> RELEVANT RESIDUES IN SEQ ID NO: (1)..(323)

<400> SEQUENCE: 10
```

Met Glu Asn Cys Pro Leu Val Ser Val Ile Val Cys Ala Tyr Asn Ala
1               5                   10                  15

Glu Gln Tyr Ile Asp Glu Ser Ile Ser Ser Ile Ile Asn Gln Thr Tyr
            20                  25                  30

Glu Asn Leu Glu Ile Ile Val Ile Asn Asp Gly Ser Thr Asp Leu Thr
        35                  40                  45

Leu Ser His Leu Glu Glu Ile Ser Lys Leu Asp Lys Arg Ile Lys Ile
    50                  55                  60

Ile Ser Asn Lys Tyr Asn Leu Gly Phe Ile Asn Ser Leu Asn Ile Gly
65                  70                  75                  80

Leu Gly Cys Phe Ser Gly Lys Tyr Phe Ala Arg Met Asp Ala Asp Asp
                85                  90                  95

Ile Ala Lys Pro Ser Trp Ile Glu Lys Ile Val Thr Tyr Leu Glu Lys
            100                 105                 110

Asn Asp His Ile Thr Ala Met Gly Ser Tyr Leu Glu Ile Ile Val Glu
        115                 120                 125

Lys Glu Cys Gly Ile Ile Gly Ser Gln Tyr Lys Thr Gly Asp Ile Trp
    130                 135                 140

Lys Asn Pro Leu Leu His Asn Asp Ile Cys Glu Ala Met Leu Phe Tyr
145                 150                 155                 160

Asn Pro Ile His Asn Asn Thr Met Ile Met Arg Ala Asn Val Tyr Arg
                165                 170                 175

Glu His Lys Leu Ile Phe Asn Lys Asp Tyr Pro Tyr Ala Glu Asp Tyr
            180                 185                 190

Lys Phe Trp Ser Glu Val Ser Arg Leu Gly Cys Leu Ala Asn Tyr Pro
        195                 200                 205

Glu Ala Leu Val Lys Tyr Arg Leu His Gly Asn Gln Thr Ser Ser Val
    210                 215                 220

Tyr Asn His Glu Gln Asn Glu Thr Ala Lys Lys Ile Lys Arg Glu Asn
225                 230                 235                 240

Ile Thr Tyr Tyr Leu Asn Lys Ile Gly Ile Asp Ile Val Ile Asn
                245                 250                 255

Ser Val Ser Leu Leu Glu Ile Tyr His Val Asp Lys Ser Asn Lys Val
            260                 265                 270

Leu Lys Ser Ile Leu Tyr Glu Met Tyr Met Ser Leu Asp Lys Tyr Thr
        275                 280                 285

Ile Thr Ser Leu Leu His Phe Ile Lys Tyr His Leu Glu Leu Phe Asp
    290                 295                 300

Leu Lys Gln Asn Leu Lys Ile Ile Lys Lys Phe Ile Arg Lys Ile Asn
305                 310                 315                 320

Val Ile Phe

```
<210> SEQ ID NO 11
<211> LENGTH: 56
<212> TYPE: DNA
<213> ORGANISM: Artificial sequence
<220> FEATURE:
<223> OTHER INFORMATION: Description of Artificial Sequence: Synthetic
``` upstream primer 1

<400> SEQUENCE: 11
gcaattattg attcggcgga tggtttgccg atggtggtgt aggctggagc tgcttc        56

<210> SEQ ID NO 12
<211> LENGTH: 58
<212> TYPE: DNA
<213> ORGANISM: Artificial sequence
<220> FEATURE:
<223> OTHER INFORMATION: Description of Artificial Sequence: Synthetic
      downstream primer

<400> SEQUENCE: 12
ctcgtcaccc tgcccggcgc gcgtgaaaat agttttcgca tatgaatatc ctccttag      58

<210> SEQ ID NO 13
<211> LENGTH: 58
<212> TYPE: DNA
<213> ORGANISM: Artificial sequence
<220> FEATURE:
<223> OTHER INFORMATION: Description of Artificial Sequence: Synthetic
      upstream primer 2

<400> SEQUENCE: 13
cactggcgat tgatatcggc ggtactaaac ttgccgccgt gtaggctgga gctgcttc      58

<210> SEQ ID NO 14
<211> LENGTH: 42
<212> TYPE: DNA
<213> ORGANISM: Artificial sequence
<220> FEATURE:
<223> OTHER INFORMATION: Description of Artificial Sequence: Synthetic
      left primer

<400> SEQUENCE: 14
ggtacctaag gaggaaaata aatgaaagaa ataaaaatac aa                       42

<210> SEQ ID NO 15
<211> LENGTH: 35
<212> TYPE: DNA
<213> ORGANISM: Artificial sequence
<220> FEATURE:
<223> OTHER INFORMATION: Description of Artificial Sequence: Synthetic
      right primer

<400> SEQUENCE: 15
ctcgagttaa gtctctaatc gattgttttc caatg                              35

<210> SEQ ID NO 16
<211> LENGTH: 20
<212> TYPE: DNA
<213> ORGANISM: Artificial sequence
<220> FEATURE:
<223> OTHER INFORMATION: Description of Artificial Sequence: Synthetic
      primer

<400> SEQUENCE: 16
caatgccaaa tatggggaac                                               20

<210> SEQ ID NO 17
<211> LENGTH: 23
<212> TYPE: DNA
<213> ORGANISM: Artificial sequence
<220> FEATURE:
<223> OTHER INFORMATION: Description of Artificial Sequence: Synthetic
      primer -continued

```
<400> SEQUENCE: 17
gcggccgcgt cttttctggc taa                                            23

<210> SEQ ID NO 18
<211> LENGTH: 425
<212> TYPE: PRT
<213> ORGANISM: Helicobacter pylori
<220> FEATURE:
<223> OTHER INFORMATION: FutA; ATCC 26695

<400> SEQUENCE: 18
```

| | | | | | | | | | | | | | | |
|---|---|---|---|---|---|---|---|---|---|---|---|---|---|---|
| Met | Phe | Gln | Pro | Leu | Leu | Asp | Ala | Phe | Ile | Glu | Ser | Ala | Ser | Ile | Glu |
| 1 | | | | 5 | | | | | 10 | | | | | 15 | |
| Lys | Met | Ala | Ser | Lys | Ser | Pro | Pro | Pro | Leu | Lys | Ile | Ala | Val | Ala |
| | | | 20 | | | | | 25 | | | | | 30 | |
| Asn | Trp | Trp | Gly | Asp | Glu | Glu | Ile | Lys | Glu | Phe | Lys | Lys | Ser | Val | Leu |
| | | | 35 | | | | | 40 | | | | | 45 | | |
| Tyr | Phe | Ile | Leu | Ser | Gln | Arg | Tyr | Ala | Ile | Thr | Leu | His | Gln | Asn | Pro |
| | 50 | | | | | 55 | | | | | 60 | | | | |
| Asn | Glu | Phe | Ser | Asp | Leu | Val | Phe | Ser | Asn | Pro | Leu | Gly | Ala | Ala | Arg |
| 65 | | | | | 70 | | | | | 75 | | | | | 80 |
| Lys | Ile | Leu | Ser | Tyr | Gln | Asn | Thr | Lys | Arg | Val | Phe | Tyr | Thr | Gly | Glu |
| | | | | 85 | | | | | 90 | | | | | 95 | |
| Asn | Glu | Ser | Pro | Asn | Phe | Asn | Leu | Phe | Asp | Tyr | Ala | Ile | Gly | Phe | Asp |
| | | | 100 | | | | | 105 | | | | | 110 | | |
| Glu | Leu | Asp | Phe | Asn | Asp | Arg | Tyr | Leu | Arg | Met | Pro | Leu | Tyr | Tyr | Ala |
| | | | 115 | | | | | 120 | | | | | 125 | | |
| His | Leu | His | Tyr | Lys | Ala | Glu | Leu | Val | Asn | Asp | Thr | Thr | Ala | Pro | Tyr |
| | 130 | | | | | 135 | | | | | 140 | | | | |
| Lys | Leu | Lys | Asp | Asn | Ser | Leu | Tyr | Ala | Leu | Lys | Lys | Pro | Ser | His | His |
| 145 | | | | | 150 | | | | | 155 | | | | | 160 |
| Phe | Lys | Glu | Asn | His | Pro | Asn | Leu | Cys | Ala | Val | Val | Asn | Asp | Glu | Ser |
| | | | | 165 | | | | | 170 | | | | | 175 | |
| Asp | Leu | Leu | Lys | Arg | Gly | Phe | Ala | Ser | Phe | Val | Ala | Ser | Asn | Ala | Asn |
| | | | 180 | | | | | 185 | | | | | 190 | | |
| Ala | Pro | Met | Arg | Asn | Ala | Phe | Tyr | Asp | Ala | Leu | Asn | Ser | Ile | Glu | Pro |
| | | | 195 | | | | | 200 | | | | | 205 | | |
| Val | Thr | Gly | Gly | Gly | Ser | Val | Arg | Asn | Thr | Leu | Gly | Tyr | Lys | Val | Gly |
| | 210 | | | | | 215 | | | | | 220 | | | | |
| Asn | Lys | Ser | Glu | Phe | Leu | Ser | Gln | Tyr | Lys | Phe | Asn | Leu | Cys | Phe | Glu |
| 225 | | | | | 230 | | | | | 235 | | | | | 240 |
| Asn | Ser | Gln | Gly | Tyr | Gly | Tyr | Val | Thr | Glu | Lys | Ile | Leu | Asp | Ala | Tyr |
| | | | | 245 | | | | | 250 | | | | | 255 | |
| Phe | Ser | His | Thr | Ile | Pro | Ile | Tyr | Trp | Gly | Ser | Pro | Ser | Val | Ala | Lys |
| | | | 260 | | | | | 265 | | | | | 270 | | |
| Asp | Phe | Asn | Pro | Lys | Ser | Phe | Val | Asn | Val | His | Asp | Phe | Asn | Asn |
| | | | 275 | | | | | 280 | | | | | 285 | | |
| Asp | Glu | Ala | Ile | Asp | Tyr | Ile | Lys | Tyr | Leu | His | Thr | His | Pro | Asn | Ala |
| | 290 | | | | | 295 | | | | | 300 | | | | |
| Tyr | Leu | Asp | Met | Leu | Tyr | Glu | Asn | Pro | Leu | Asn | Thr | Leu | Asp | Gly | Lys |
| 305 | | | | | 310 | | | | | 315 | | | | | 320 |
| Ala | Tyr | Phe | Tyr | Gln | Asp | Leu | Ser | Phe | Lys | Lys | Ile | Leu | Asp | Phe | Phe |
| | | | | 325 | | | | | 330 | | | | | 335 | |
| Lys | Thr | Ile | Leu | Glu | Asn | Asp | Thr | Ile | Tyr | His | Lys | Phe | Ser | Thr | Ser |
| | | | 340 | | | | | 345 | | | | | 350 | | |

```
Phe Met Trp Glu Tyr Asp Leu His Lys Pro Leu Val Ser Ile Asp Asp
        355                 360                 365

Leu Arg Val Asn Tyr Asp Asp Leu Arg Val Asn Tyr Asp Arg Leu Leu
370                 375                 380

Gln Asn Ala Ser Pro Leu Leu Glu Leu Ser Gln Asn Thr Thr Phe Lys
385                 390                 395                 400

Ile Tyr Arg Lys Ala Tyr Gln Lys Ser Leu Pro Leu Leu Arg Ala Val
                405                 410                 415

Arg Lys Leu Val Lys Lys Leu Gly Leu
        420                 425

<210> SEQ ID NO 19
<211> LENGTH: 476
<212> TYPE: PRT
<213> ORGANISM: Helicobacter pylori
<220> FEATURE:
<223> OTHER INFORMATION: FutB; HP 0651; ATCC 26695

<400> SEQUENCE: 19

Met Phe Gln Pro Leu Leu Asp Ala Phe Ile Glu Ser Ala Ser Ile Glu
1               5                   10                  15

Lys Met Val Ser Lys Ser Pro Pro Pro Leu Lys Ile Ala Val Ala
            20                  25                  30

Asn Trp Trp Gly Asp Glu Glu Ile Lys Glu Phe Lys Lys Ser Val Leu
        35                  40                  45

Tyr Phe Ile Leu Ser Gln Arg Tyr Ala Ile Thr Leu His Gln Asn Pro
    50                  55                  60

Asn Glu Ser Ser Asp Leu Val Phe Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Ala
        115                 120                 125

His Leu His Tyr Glu Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys
            260                 265                 270

Asp Phe Asn Pro Lys Ser Phe Val Asn Val His Asp Phe Asn Asn Phe
        275                 280                 285

Asp Glu Ala Ile Asp Tyr Ile Lys Tyr Leu His Thr His Pro Asn Ala
```

-continued

| | | | | 290 | | | | 295 | | | | 300 | | |
|---|---|---|---|---|---|---|---|---|---|---|---|---|---|---|
| Tyr | Leu | Asp | Met | Leu | Tyr | Glu | Asn | Pro | Leu | Asn | Thr | Leu | Asp | Gly | Lys |
| 305 | | | | | 310 | | | | 315 | | | | | | 320 |
| Ala | Tyr | Phe | Tyr | Gln | Asp | Leu | Ser | Phe | Lys | Lys | Ile | Leu | Asp | Phe | Phe |
| | | | | 325 | | | | | 330 | | | | | 335 | |
| Lys | Thr | Ile | Leu | Glu | Asn | Asp | Thr | Ile | Tyr | His | Asn | Asn | Pro | Phe | Ile |
| | | | 340 | | | | | 345 | | | | | 350 | | |
| Phe | Tyr | Arg | Asp | Leu | His | Glu | Pro | Leu | Ile | Ser | Ile | Asp | Asp | Leu | Arg |
| | | 355 | | | | | 360 | | | | | 365 | | | |
| Val | Asn | Tyr | Asp | Asp | Leu | Arg | Val | Asn | Tyr | Asp | Asp | Leu | Arg | Val | Asn |
| | 370 | | | | | 375 | | | | | 380 | | | | |
| Tyr | Asp | Asp | Leu | Arg | Val | Asn | Tyr | Asp | Asp | Leu | Arg | Val | Asn | Tyr | Asp |
| 385 | | | | | 390 | | | | 395 | | | | | | 400 |
| Asp | Leu | Arg | Val | Asn | Tyr | Asp | Asp | Leu | Arg | Val | Asn | Tyr | Asp | Asp | Leu |
| | | | | 405 | | | | | 410 | | | | | 415 | |
| Arg | Val | Asn | Tyr | Asp | Asp | Leu | Arg | Val | Asn | Tyr | Asp | Asp | Leu | Arg | Val |
| | | | 420 | | | | | 425 | | | | | 430 | | |
| Asn | Tyr | Asp | Arg | Leu | Leu | Gln | Asn | Ala | Ser | Pro | Leu | Leu | Glu | Leu | Ser |
| | | 435 | | | | | 440 | | | | | 445 | | | |
| Gln | Asn | Thr | Thr | Phe | Lys | Ile | Tyr | Arg | Lys | Ala | Tyr | Gln | Lys | Ser | Leu |
| | 450 | | | | | 455 | | | | | 460 | | | | |
| Pro | Leu | Leu | Arg | Thr | Ile | Arg | Arg | Trp | Val | Lys | Lys | | | | |
| 465 | | | | | 470 | | | | | 475 | | | | | |